(12) United States Patent
Volodarsky et al.

(10) Patent No.: US 11,129,417 B2
(45) Date of Patent: Sep. 28, 2021

(54) PORTABLE VAPORIZING DEVICE, CARTRIDGE AND METHODS

(71) Applicant: Puff Corporation, Los Angeles, CA (US)

(72) Inventors: Roger Volodarsky, Los Angeles, CA (US); Avinash Bajpai, Los Angeles, CA (US); Roger Sayre, Los Angeles, CA (US)

(73) Assignee: Puff Corporation, Los Angeles, CA (US)

( * ) Notice: Subject to any disclaimer, the term of this patent is extended or adjusted under 35 U.S.C. 154(b) by 0 days.

(21) Appl. No.: 16/665,259

(22) Filed: Oct. 28, 2019

(65) Prior Publication Data

US 2020/0077709 A1 Mar. 12, 2020

Related U.S. Application Data

(63) Continuation of application No. PCT/US2019/049858, filed on Sep. 6, 2019.

(60) Provisional application No. 62/728,512, filed on Sep. 7, 2018.

(51) Int. Cl.
| | |
|---|---|
| *A24F 40/485* | (2020.01) |
| *F16K 99/00* | (2006.01) |
| *A24F 40/46* | (2020.01) |
| *A61M 15/00* | (2006.01) |
| *A61M 15/06* | (2006.01) |
| *A61M 11/04* | (2006.01) |
| *A24F 40/10* | (2020.01) |

(52) U.S. Cl.
CPC ............ *A24F 40/485* (2020.01); *A24F 40/46* (2020.01); *A61M 15/0025* (2014.02); *A61M 15/06* (2013.01); *F16K 99/0025* (2013.01); *A24F 40/10* (2020.01); *A61M 11/042* (2014.02); *A61M 11/044* (2014.02); *A61M 2205/3368* (2013.01); *A61M 2205/3653* (2013.01); *A61M 2205/8206* (2013.01)

(58) Field of Classification Search
CPC ...... A24F 47/008; A24F 40/485; A24F 40/48; A24F 40/44
See application file for complete search history.

(56) References Cited

U.S. PATENT DOCUMENTS

| | | | |
|---|---|---|---|
| 5,353,813 A | * | 10/1994 | Deevi ................... A24F 47/008 |
| | | | 131/194 |
| D492,061 S | | 6/2004 | Reynolds |
| D760,429 S | | 6/2016 | Emarlou |

(Continued)

OTHER PUBLICATIONS

Patent Cooperation Treaty, International Search Report for PCT/US2019/049858, 3 pages dated Nov. 4, 2019.

(Continued)

*Primary Examiner* — Michael H. Wilson
(74) *Attorney, Agent, or Firm* — Bryan Cave Leighton Paisner LLP

(57) ABSTRACT

A portable vaporizing device and/or cartridge comprises a product chamber capable of holding a vaporizable product therein, and a porous valve element configured to be heated to flow the vaporizable product therethrough and generate vapor from the vaporizable product, and optionally including a heat transfer element to heat the vaporizable product as it flows through the product chamber towards the porous valve element.

21 Claims, 23 Drawing Sheets

(56) References Cited

U.S. PATENT DOCUMENTS

| | | | |
|---|---|---|---|
| 9,609,894 B2* | 4/2017 | Abramov | A24F 47/008 |
| 9,648,909 B2 | 5/2017 | Zhou et al. | |
| 10,080,387 B2 | 9/2018 | Phillips et al. | |
| 10,092,041 B1 | 10/2018 | Rinehart et al. | |
| D833,064 S | 11/2018 | Verleur et al. | |
| D834,746 S | 11/2018 | Liu et al. | |
| 10,117,461 B2 | 11/2018 | Chen | |
| 10,130,122 B2 | 11/2018 | Anderson | |
| 10,136,679 B1 | 11/2018 | Shotey et al. | |
| 10,159,282 B2 | 12/2018 | Monsees et al. | |
| D843,650 S | 3/2019 | Verleur et al. | |
| D861,147 S | 9/2019 | He et al. | |
| 2014/0109921 A1 | 4/2014 | Chen | |
| 2015/0136124 A1* | 5/2015 | Aronie | A24F 47/008 128/202.21 |
| 2015/0136127 A1 | 5/2015 | Dimatteo | |
| 2016/0295915 A1 | 10/2016 | Jochnowitz et al. | |
| 2017/0233114 A1 | 8/2017 | Christensen et al. | |
| 2017/0238617 A1 | 8/2017 | Scatterday | |
| 2017/0340011 A1* | 11/2017 | Batista | A24F 47/008 |
| 2018/0029782 A1* | 2/2018 | Zuber | A24F 47/008 |
| 2018/0064170 A1* | 3/2018 | Peuchert | H05B 3/265 |
| 2018/0110263 A1* | 4/2018 | Borkovec | A24F 47/004 |
| 2018/0132534 A1 | 5/2018 | Reevell | |
| 2018/0132535 A1 | 5/2018 | Reevell | |
| 2018/0160737 A1 | 6/2018 | Verleur et al. | |
| 2018/0177240 A1 | 6/2018 | Duque et al. | |
| 2018/0272083 A1 | 9/2018 | Avots | |
| 2018/0289909 A1 | 10/2018 | Lindars et al. | |
| 2019/0008206 A1* | 1/2019 | Gimkiewicz | G06K 9/209 |
| 2019/0098933 A1* | 4/2019 | Courbat | A24F 47/008 |
| 2019/0166913 A1* | 6/2019 | Trzecieski | A61M 11/042 |
| 2019/0223504 A1* | 7/2019 | Chen | A24F 47/00 |
| 2019/0373953 A1* | 12/2019 | Atkins | A61M 15/06 |
| 2020/0054077 A1* | 2/2020 | Chen | F16J 15/021 |

OTHER PUBLICATIONS

Vaporizer Chief, LLC, Pulsar APX Vape, retrieved from www.vaporizerchief.com/pulsar-apx-vape-v2/ 2020.

* cited by examiner

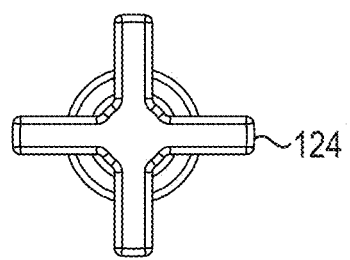
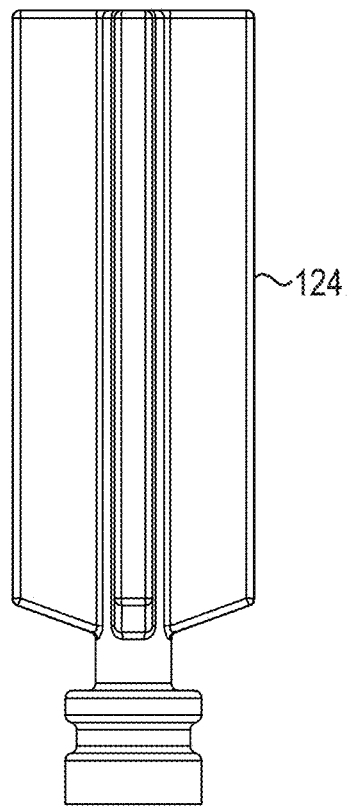
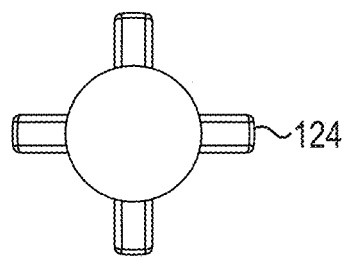
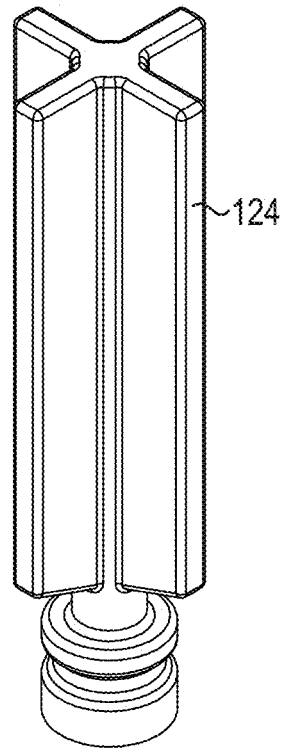
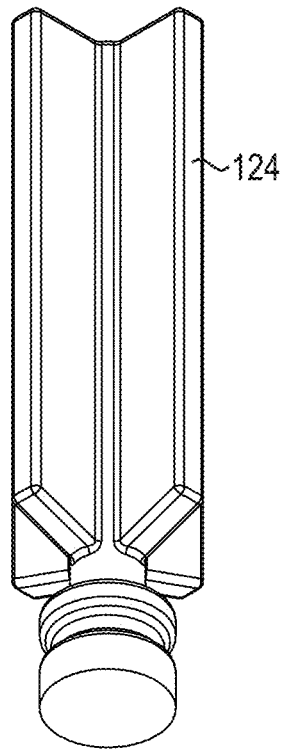
FIG. 2A                FIG. 2B

PORTABLE VAPORIZING DEVICE, CARTRIDGE AND METHODS

CROSS REFERENCE TO RELATED APPLICATIONS

This application claims the benefit of priority as a by-pass continuation application from PCT Application Serial No. PCT/US19/49858, filed on Sep. 6, 2019, which claims benefit of priority from U.S. Provisional Application Ser. No. 62/728,512 filed on Sep. 7, 2018, each of which is hereby incorporated by reference herein in its entirety.

FIELD OF THE INVENTION

Aspects of the present invention relate to a cartridge for use with a vaporizable product, as well as a portable vaporizing device configured to accept the portable cartridge to generate an inhalable vapor therefrom, and methods of use and manufacture therefore.

BACKGROUND

Electronic portable vaporizers are used for aroma and/or inhalation therapy of vaporized oils such as cannabis, lavender, chamomile or any other plant material. More specifically, "pre-fill" vaporizers include cartridges containing a heating element and fibrous wick, usually cotton. By capillary action, which is the ability of a liquid to flow in narrow spaces without the assistance of external forces like gravity, the oil is moved from a wet area through the fibrous material to a dry area in which the oil can be vaporized by the heating element before inhalation. Vaporizers are regarded by the public as one of the easiest and healthiest ways to inhale cannabis; however the current technology used in pre-filled vaporizers results in a decrease in both quality of oil and in overall health benefit.

In the pre-fill vaporizer industry, a common problem that is encountered is that the cannabis product intended for inhalation is produced in a solid or semi-solid form, and/or may simply be too viscous to be moved through a wick via capillary action out of the wet chamber. One means of addressing this problem is to add substances that can thin the cannabis product, such as propylene glycol (PG), which is used as a thinning agent and/or diluent in a number of products. However, it is believed that such substances added to the cannabis product can have a deleterious effect on the lungs upon inhalation thereof, and thus are best avoided.

Pre-filled vaporizer cartridges are one of the most popular products for inhalation of cannabis products. They are user friendly, discrete, and generally regarded as a healthy alternative to smoking. However, for the reasons described above, current pre-filled vaporizers suffer from limitations in terms of the types of cannabis products that can be safely used, and the quality of experience with these products.

Accordingly, there is a need for portable vaporizers and/or cartridges therefor that expand the range of cannabis products that can be satisfactorily vaporized and inhaled, without requiring the addition of potentially dangerous additives to "thin" the products. There is also a need for portable vaporizers and/or cartridges that provide an improved experience in the inhalation of highly viscous and/or semi-solid products that have previously been difficult to convert to a vaporized form, and/or that are not capable of being readily absorbed into a wicking material.

SUMMARY

According to one embodiment, a portable vaporizing device comprises a vaporizable product receiving chamber configured to receive a vaporizable product therein, the vaporizable product receiving chamber comprising one or more chamber walls defining an product flow path between upper and lower opposing ends of the vaporizable product receiving chamber; a heat transfer element extending at least partly along the product flow path, and configured to transfer heat to vaporizable product received in the product receiving chamber to at least partially melt and/or reduce the viscosity of vaporizable product as it flows via gravitational pull from the upper end to the lower end along the product flow path; and a porous valve element located towards the lower end of the vaporizable product receiving chamber, the porous valve element comprising a porous valve body comprising porous material configured to allow heated vaporizable product having a predetermined viscosity to pass therethrough; at least one first porous entry surface of the porous valve body configured to receive the heated vaporizable product from the product flow path into the porous valve body; and at least one porous vaporizing surface of the porous valve body configured to flow the heated vaporizable product out of the porous valve body, wherein the heat transfer element and porous valve element are configured to be placed in thermal contact with at least one heating element to provide heating of the heat transfer element and porous valve element during operation of the portable vaporizing device to heat the vaporizable product to the predetermined viscosity, wherein the porous valve element is configured to be heated by the at least one heating element to cause the heated vaporizable product having the predetermined viscosity from the product receiving chamber to flow into and through the porous valve body, and to cause the heated vaporizable product to at least partially vaporize in the vicinity of the at least one porous vaporizing surface while exiting the porous valve body, and wherein the porous valve body comprises a thermal conductivity of at least 0.5 W/m*K to retain and transfer heat to the vaporizable product.

According to yet another embodiment, a portable vaporizing device comprises a vaporizable product receiving chamber configured to receive a vaporizable product therein, the vaporizable product receiving chamber comprising one or more chamber walls defining a product flow path between upper and lower opposing ends of the vaporizable product receiving chamber; and a porous valve element located towards the lower end of the vaporizable product receiving chamber that is configured to heat the vaporizable product to a predetermined viscosity, the porous valve element comprising: a porous valve body comprising porous material configured to allow heated vaporizable product having the predetermined viscosity to pass therethrough; at least one exposed first porous entry surface of the porous valve body that is configured to be placed in direct thermal contact with vaporizable product in the product chamber to transfer heat thereto, the at least one first porous entry surface being configured to receive the heated vaporizable product from the product flow path into the porous valve body, and the exposed first porous entry surface comprising a porous material having a thermal conductivity of at least 0.5 W/m*K; and at least one porous vaporizing surface configured to flow the heated vaporizable product therethrough such that the vaporizable product is at least partially vaporized in the vicinity of the at least one porous vaporizing surface while exiting the porous valve body, wherein a portion of the at least one porous vaporizing surface is on a side of the porous valve body opposite the first porous entry surface, and the portion of at least one porous vaporizing surface is configured to be placed into direct contact with at least one heating element to provide heating of the porous valve element during operation of the portable vaporizing device.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-2B are profile views of an embodiment of a heat transfer element according to aspects herein;

DETAILED DESCRIPTION OF THE INVENTION

Aspects of the invention as described herein are directed to a portable vaporizing device 100 for forming an inhalable vapor from vaporizable products, such as aromatic products, therapeutic products and/or products with physiological effects. Examples of such products can include herbs, such as tobacco, cannabis, lavender, chamomile, and other types of plant material. In one embodiment, a vaporizable product can comprise a cannabinoid, such as for example one or more of cannabidiol (a generally non-psychoactive therapeutic substance) and tetrahydrocannabinol (THC) (a psychoactive therapeutic substance). The vaporizable products may in some embodiments be in the form of an oil and/or wax product comprising the vaporizable products, e.g., as extracted from plant material containing the products, and may optionally be provided in combination with carriers or other additives. According to one aspect, the vaporizable products may be hash, which is a viscous resin containing tetrahydrocannabinol and other cannabinoids, extracted from the cannabis plant. According to yet another aspect, the vaporizable products may be cannabidiol in an oil or other liquid form. According to yet a further aspect, the vaporizable products can comprise a distillate product formed by distillation of an extract from the cannabis plant, typically in an oil and/or liquid form. In certain embodiments, the vaporizable product may be one that has a relatively high viscosity, such as a product having a viscosity of at least 5 Poise, and even at least 10 Poise or higher at room temperature.

Referring to FIGS. 1A-1C and 13A-13B, embodiments of a portable vaporizing device 100 for inhalation of a vaporizable product are shown. The device 100 comprises a vaporizable product receiving chamber 114 configured to receive a vaporizable product therein. According to certain embodiments, the device 100 is capable of being used with one or more cartridges 112 having the product receiving chamber 114 therein. The cartridges 112 may be removable and/or refillable, or can comprise single-use cartridges. In another embodiment, the device 100 can comprise a permanent product receiving chamber incorporated into the structure thereof, and which is not intended for removal from the device 100 but that may optionally be refilled with product. According to yet another embodiment, the cartridge itself can be considered to be a portable vaporizing device 100, that can be utilized either by itself (e.g., in an embodiment where the cartridge contains a built in heater), or with a complementary device to provide heating of the product within the cartridge 112 and any other components to facilitate inhalation of the vapor formed from the vaporizable product.

Figure 1A:
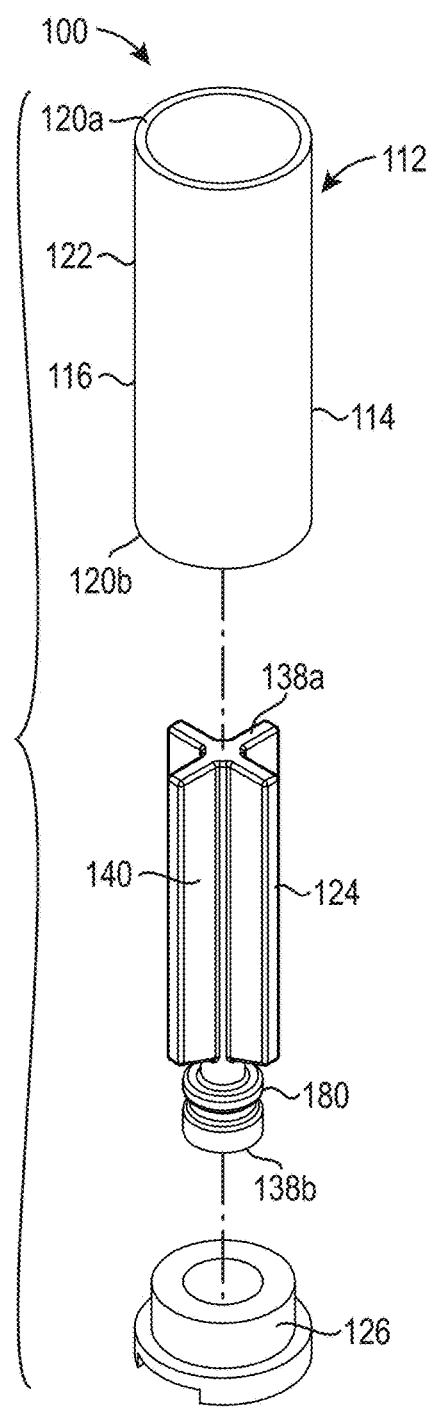
FIGS. 1A-1C are exploded views of an embodiment of a cartridge for a vaporizable product, according to aspects herein.
Figure 1B:
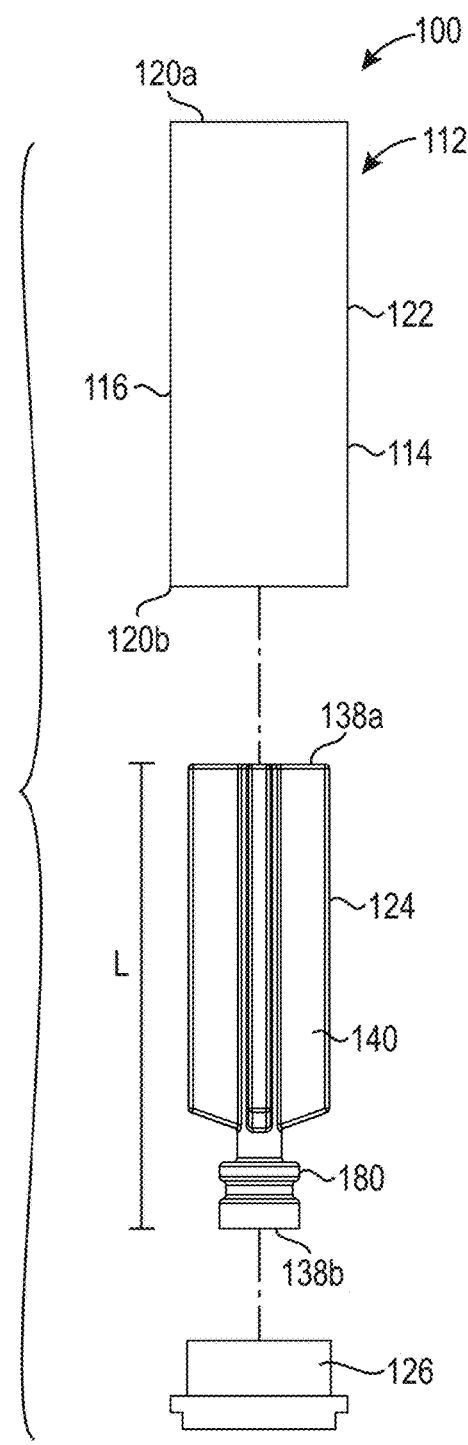
Figure 1C:
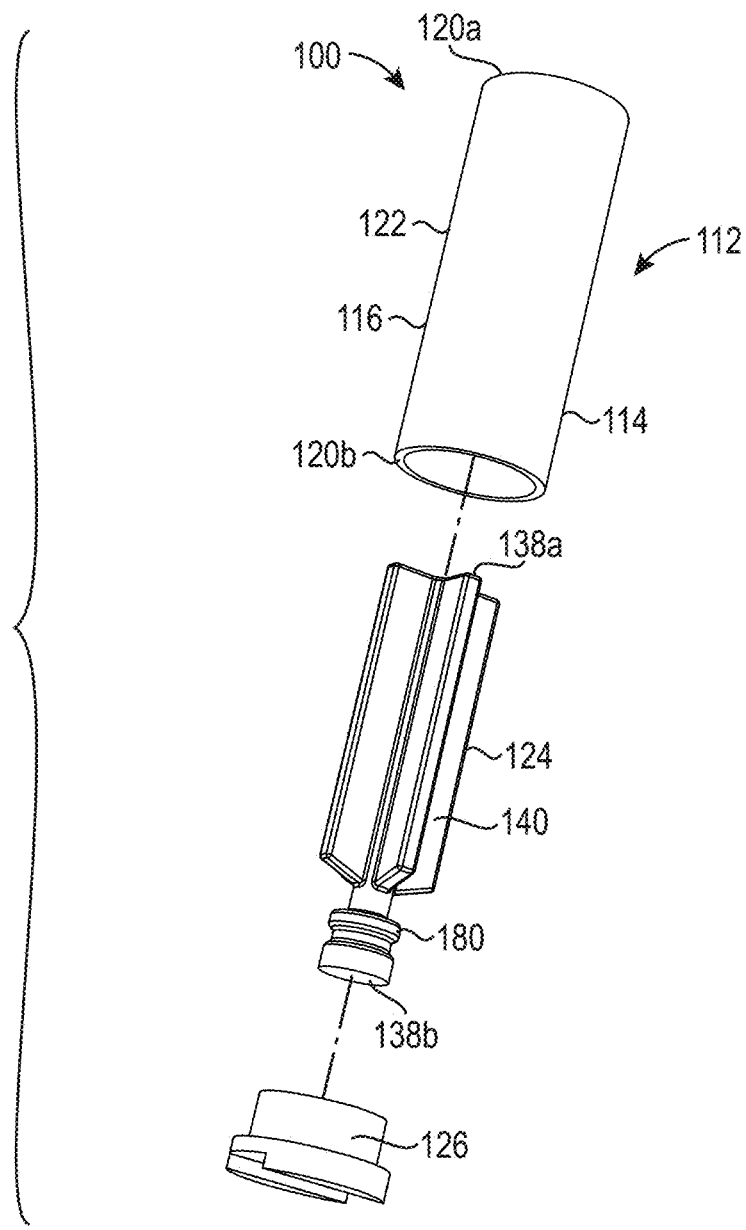
Figure 3A:
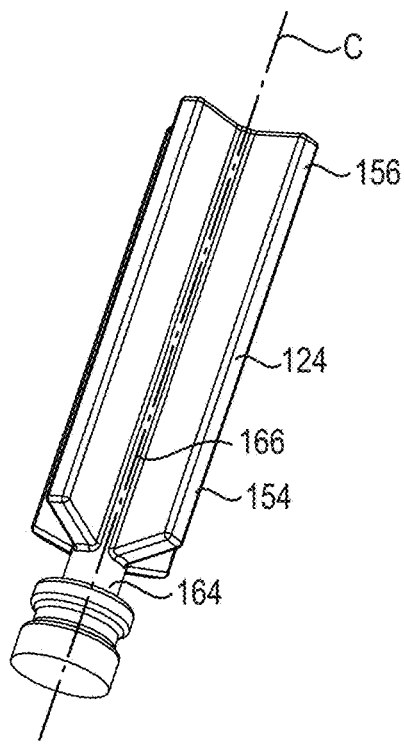
FIGS. 3A-3C are isometric views of different embodiments of heat transfer elements for a vaporizable product, according to aspects herein.
Figure 3B:
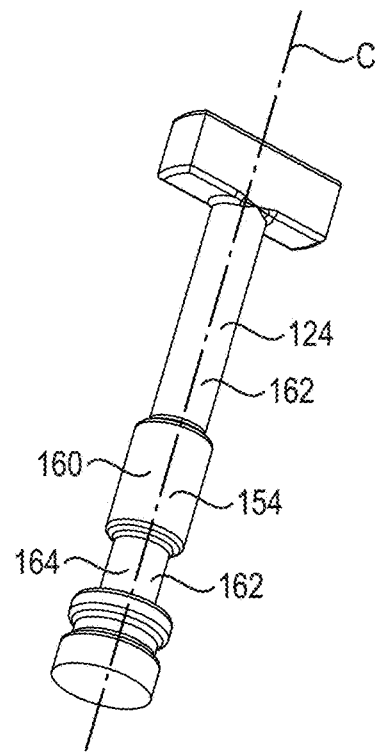
Figure 3C:
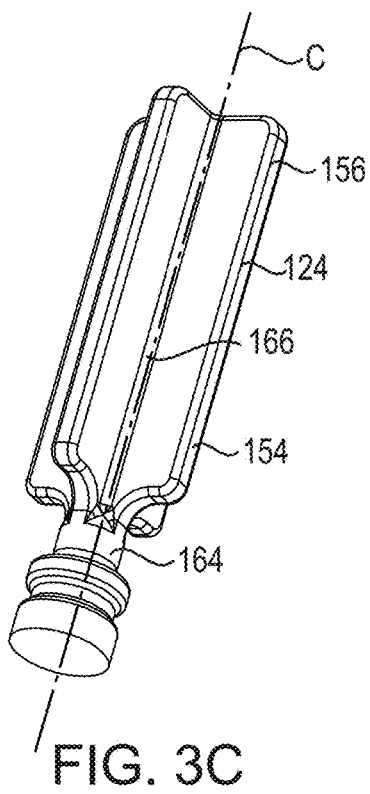
Figure 4A:
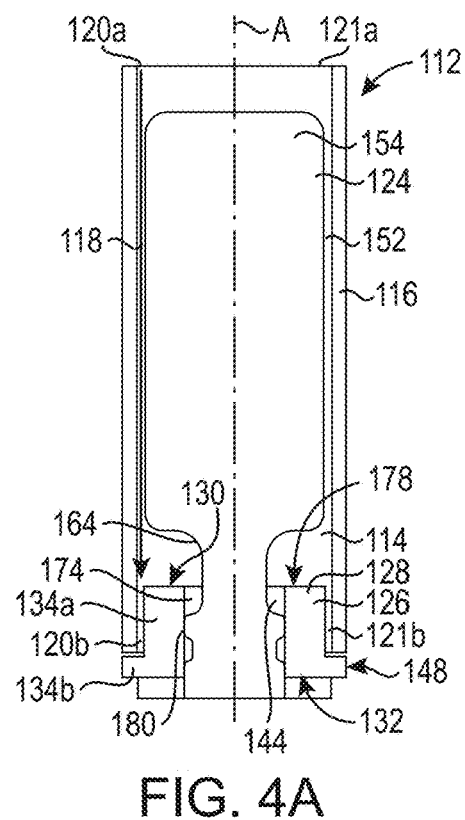
FIGS. 4A-4C are sectional views of different embodiments of cartridges according to aspects herein.
Figure 4B:
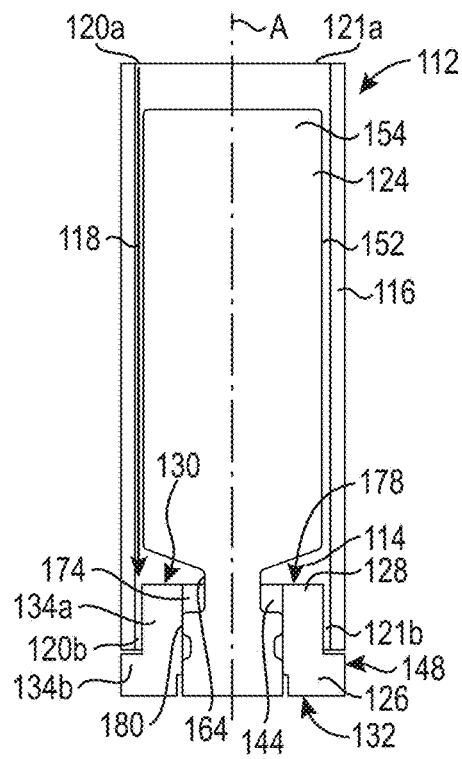
Figure 4C:
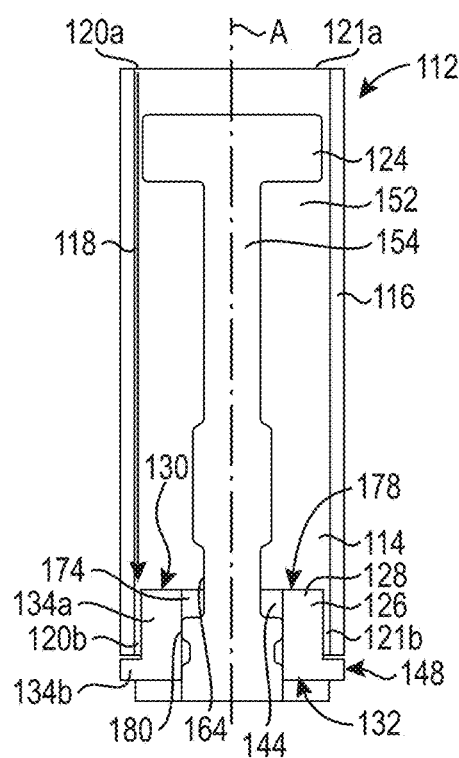
Figure 5A:
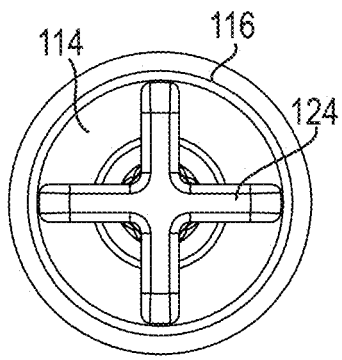
FIGS. 5A-5C are top views of the cartridge embodiments depicted in FIGS. 4A-4C.
Figure 5B:
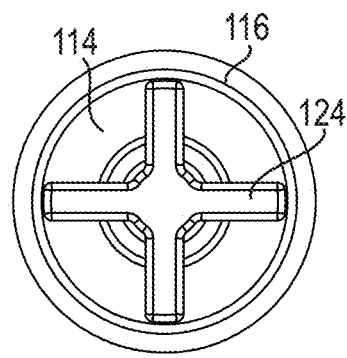
Figure 5C:
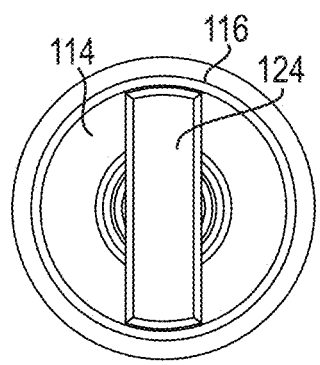
Figure 6A:
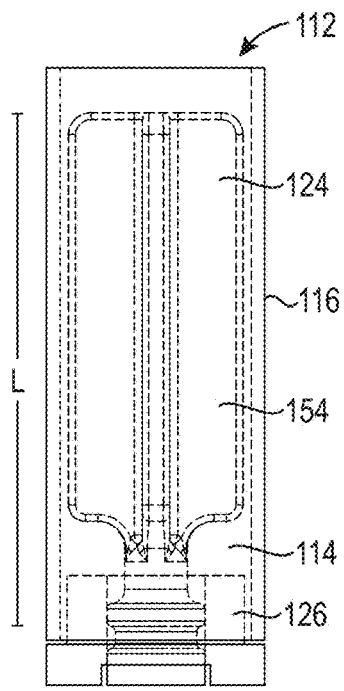
FIGS. 6A-6C are side views of the cartridge embodiments depicted in FIGS. 4A-4C.
Figure 6B:
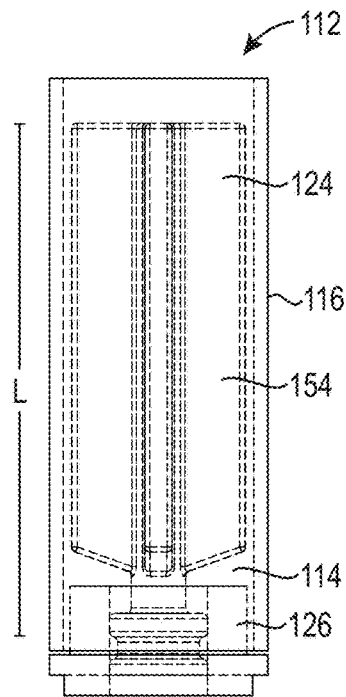
Figure 6C:
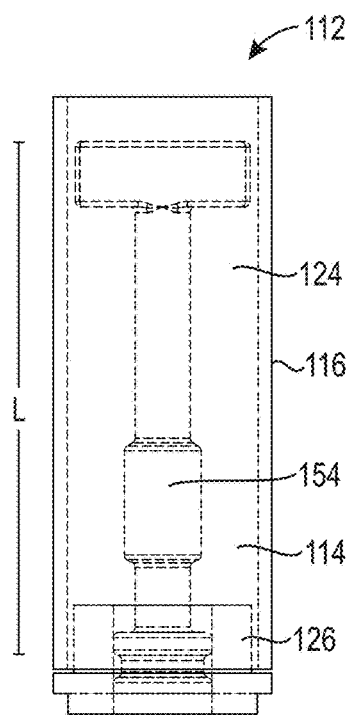
Figure 7A:
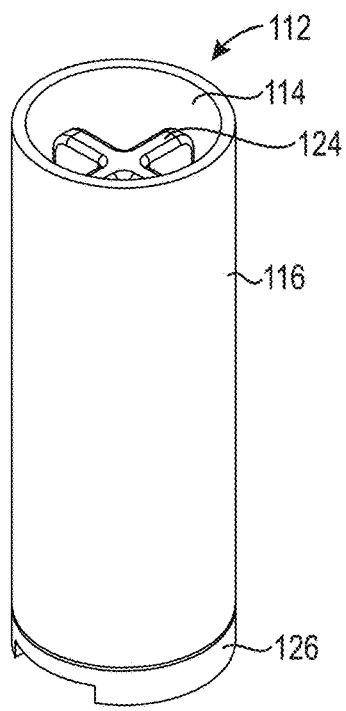
FIGS. 7A-7C are isometric views of the cartridge embodiments depicted in FIGS. 4A-4C.
Figure 7B:
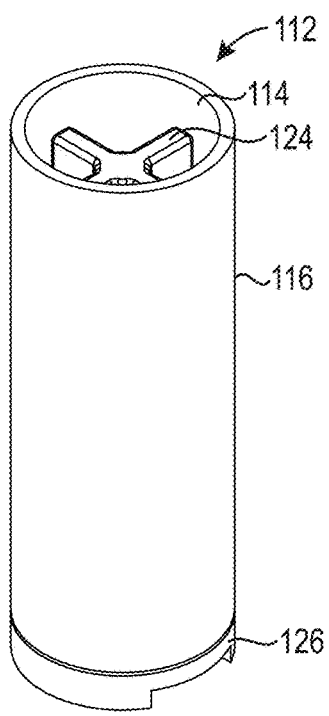
Figure 7C:
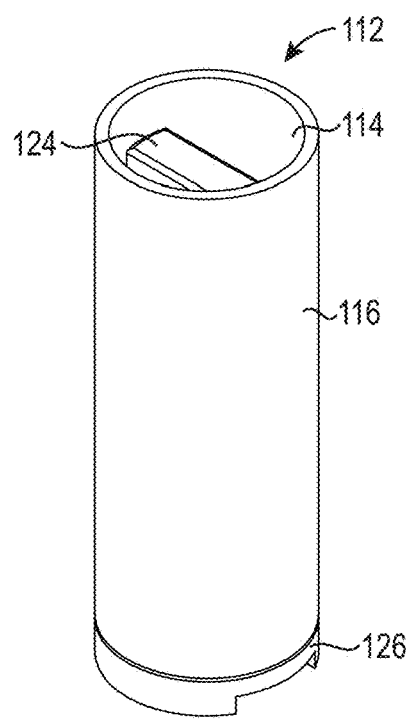
Figure 8A:
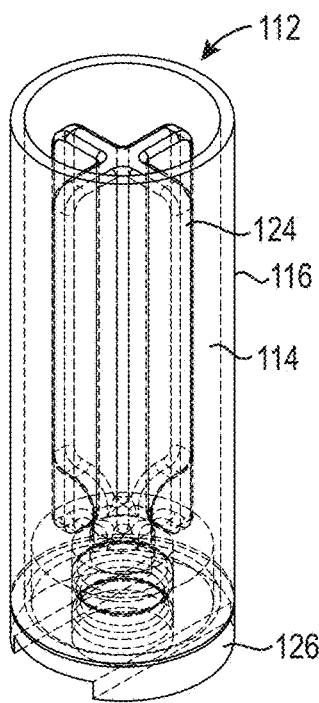
FIGS. 8A-8C are alternative isometric views of the cartridge embodiments depicted in FIGS. 7A-7C.
Figure 8B:
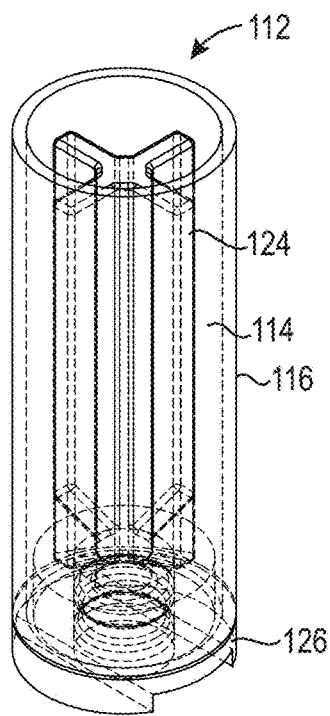
Figure 8C:
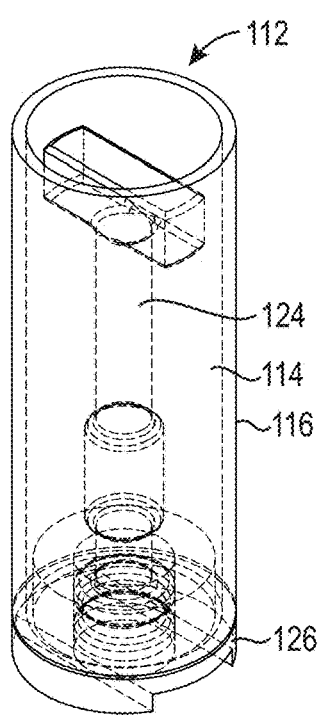
Figure 9A:
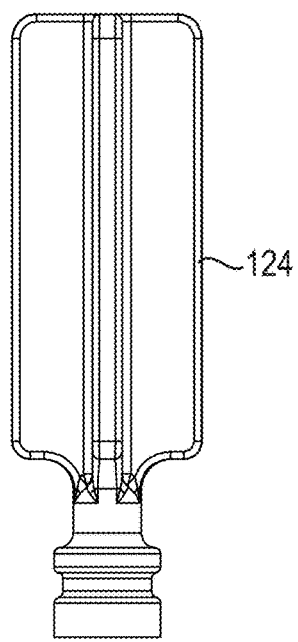
FIGS. 9A-9C are profile views of different embodiments of heat transfer elements according to aspects herein.
Figure 9B:
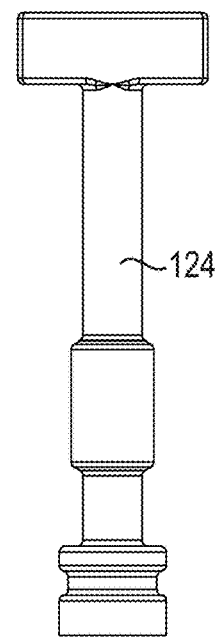
Figure 9C:
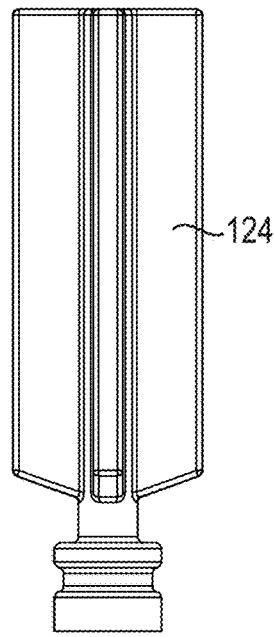

Referring to the embodiments as shown in FIGS. 1A-9C, the portable vaporizing device 100 and/or cartridge 112 comprises the vaporizable product receiving chamber 114 comprises one or more chamber walls 116 defining an product flow path 118 between upper and lower opposing ends 120a, 120b of the vaporizable product receiving chamber (see, e.g., FIGS. 1A-1C and 4A-4C). In the embodiments as shown in FIGS. 1A-1C, the chamber walls 116 comprise sidewalls 122 in a tube shape surrounding a circumference of the product receiving chamber 114, although other shapes for the sidewalls may also be provided, such as rectangular, prismatic, or irregular shapes. The chamber walls 116 can further define an upper opening 121*a* of the product chamber at the upper end 120*a* of the chamber 114, and a lower opening 121*b* at the lower end 120*b* of the product chamber 114 (see, e.g., FIGS. 4A-4C). The product flow path 118 generally extends from the upper end 120*a* of the product chamber 114 to the lower end 120*b* of the product chamber, and corresponds to the path taken by the product in the chamber as it moves via gravitational pull from the upper to the lower end of the product chamber. While the product flow path 118 as shown in FIGS. 4A-4C is depicted as being fairly linear from the top to the bottom end of the product chamber, the product flow path 118 can also in certain embodiments be convoluted, such as in a spiral, zig-zag, or other flow architecture, according to a design of the device 100. According to certain embodiments, the product chamber may be configured such that it can be filled with vaporizable product at the upper opening 121*a*, and such that the vaporizable product flows upon activation of the vaporizing device 100 towards the lower opening 121*b*.

Referring again to the embodiments of FIGS. 1A-1C and 4A-4C, the device 100 and/or cartridge 112 can comprise a heat transfer element 124 that extends at least partly along the product flow path 118 in the product chamber 114. The heat transfer element 124 is configured to transfer heat to a vaporizable product received in the product receiving chamber 114, to at least partially melt and/or reduce the viscosity of vaporizable product as it flows via gravitational pull from the upper end 120*a* to the lower end 120*b* of the chamber 114 along the product flow path 118. That is, in the case of vaporizable substances such as hash, cannabidiol and/or distillate, or other flowable substances, the heat transfer element 124 may be capable of heating the product within the product chamber 114, such that the product can be made flowable and/or be maintained in a flowable form as it passes along the product flow path 118. The flow path may be a substantially linear flow path, or can comprise a convoluted flow path from the upper end to the lower end of the product chamber.

According to certain embodiments, the device 100 and/or cartridge 112 comprises a porous valve element 126 located towards the lower end 120*b* of the chamber 114. The porous valve element 126 may form at least a portion of a bottom wall of the product receiving chamber 114, to contain the vaporizable product within the chamber 114 when the device 100 is not in operation. Referring to FIGS. 4A-4C and 10, the porous valve element 126 comprises a porous valve body 128 formed of a porous material configured to allow heated vaporizable product having a predetermined viscosity to pass therethrough.

That is, according to certain embodiments, the porous valve body 128 may have a porosity and/or pore size that allows vaporizable product to pass thorough the pores of the body when the product reaches a sufficiently low viscosity through heating thereof, or the product otherwise has a sufficiently low viscosity. For products such as distillate, the amount of heating required may be relatively little, as the viscosity of the product drops quickly with increasing temperature. However, for higher viscosity products, such as for example hash and cannabidiol, heating to higher temperatures may be required to reach a sufficiently low viscosity. In this way, in certain embodiments, the porous valve body 128 may act as a valve structure that allows product therethrough when an appropriately low viscosity is achieved, but contains product within the chamber when the viscosity exceeds a predetermined viscosity at which the product is able to pass through the pores of the porous valve body. In alternative embodiments, such as for very low viscosity products capable of passing through the porous valve body at room temperature or with substantially no heating, an alternative mechanism for containing a flow of the product from the chamber may be provided. The porous valve element 126 can absorb product having the predetermined viscosity via capillary action, and this capillary action may also serve to contain the product within or outside of the porous valve element 126 when it is not activated (e.g., when it is not being heated)

Referring again to the embodiments as shown in FIGS. 4A-4C and 10, the porous valve element 126 further comprises at least one first porous entry surface 130 of the porous valve body 128 configured to receive the heated vaporizable product from the product flow path 118 into the porous valve body 128. As depicted in the embodiments of FIGS. 4A-4C, the first porous entry surface comprises a substantially planar surface that is configured to contact the product at the lower end 120*b* of the product chamber 114, although alternative embodiments for the first entry surface may also be provided. The porous valve element 126 also comprises at least one porous vaporizing surface 132 of the porous valve body 128 that is configured to flow the heated vaporizable product out of the porous valve body 128. In the embodiment shown in FIGS. 4A-4C and 10, at least a portion of the porous vaporizing surface 132 is on an opposite side of the valve body 128 from the first porous entry surface 130.

Furthermore, in the embodiment as depicted in these FIGS. 4A-4C, at least a portion of the porous valve body 128 is configured to be fitted within the walls 116 of the product chamber 114, and at least a portion of the porous valve body 128 extends beyond the walls 116 of the product chamber 124, such that least a portion of the porous vaporizing surface 132 may extend beyond the walls 116 of the product chamber. In the embodiment as shown in FIGS. 4A-4C, the porous valve body comprises an upper portion 134*a* that is sized to fit within the walls 116, and a lower portion 134*b* that extends beyond the walls 116 and also has a greater width than the walls 116. For example, the lower portion 134*b* may form a lower lip that extends both below and beyond a width of the walls 116. In the embodiment shown in FIGS. 4A-4C and 10, the valve body 128 comprises a generally annular shape, with an upper portion 134*a* comprising an upper ring-shaped portion having a first diameter sized to fit within the walls 116, and a lower portion 134*b* comprising an lower ring-shaped portion having a second diameter than is larger than the first, and that exceeds a diameter of the walls 116. For example, the lower ends of the walls 116 may abut a top surface of the lower portion of the valve body, such that it can act to plug the lower end of the product chamber 114. Other configurations and/or shapes may also be provided, such as rectangular and/or square shapes for the wall and/or valve body cross-section.

Referring to FIGS. 12A-12D, according to embodiments herein, at least one or both of the heat transfer element 124 and porous valve element 126 are configured to be placed in thermal contact with at least one heating element 136, such as the same or different heating elements 136. In one embodiment, the at least one heating element 136 may be a part of a removable cartridge 112 that is provided to the vaporizing device. That is, the at least one heating element 136 may be removable as a part of the cartridge from the vaporizing device 100. In another embodiment, the heating element 136 forms a part of the vaporizing device 100, and a removable cartridge 112 having the porous valve element 126 and/or heat transfer element is configured to be received within the vaporizing device in a configuration such that the porous valve element 126 and/or heat transfer element 124 are placed into thermal contact with the at least one heating element 136 in the vaporizing device 100 (see, e.g., FIG. 13A).

According to embodiments herein, one or both of the heat transfer element 124 and porous valve element 126 can be placed into thermal communication with the at least one heating element 136 to provide heating of the heat transfer element 124 and porous valve element 136 during operation of the portable vaporizing device 100, such as to heat the vaporizable product to the predetermined viscosity at which the vaporizable product is capable of flowing through the porous valve element, and/or to provide a predetermined rate of flow through the porous valve element 126. For example, the porous valve element 126 can be configured to be heated by the at least one heating element 136 to cause the heated vaporizable product having the predetermined viscosity from the product receiving chamber 114 to flow into and through the porous valve body 128. The porous valve element 126 can also be configured such that the heated vaporizable product flowing through the porous valve body at least partially vaporize in the vicinity of the at least one porous vaporizing surface 132 while exiting the porous valve body 128, thereby creating a vaporized product suitable for inhalation. In one embodiment, one or both of the porous valve element and heat transfer element are placed into direct physical contact with the at least one heating element, which may be the same or different heating elements, in order to transfer heat from the heating element(s) to the porous valve element and heat transfer element.

According to one embodiment, the heat transfer element 124 is configured to be heated by the at least one heating element 136 at a position of the heat transfer element 124 along the product flow path 118 to a predetermined temperature of at least 125° F., and even higher, to provide the predetermined viscosity of the vaporizable product in the chamber 114. For example, according to certain embodiments, the heat transfer element is configured to be heated at the position along the product flow path to a predetermined temperature of at least 125° F., at least 135° F., a least 145° F., at least 150° F., at least 165° F., at least 170° F., at least 180° F., at least 195° F., at least 200° F., at least 215° F., at least 225° F., and/or at least 250° F., to heat the vaporizable product in the product chamber. Furthermore, according to one embodiment, the heat transfer element 124 is configured to be heated at the position along the product flow path 118 to the predetermined temperature within a time period of no more than 10 seconds, no more than 25 seconds, no more than 50 seconds, no more than 75 seconds, no more than 100 second, and/or no more than 150 seconds. In one embodiment, the predetermined temperature may be obtained within 1 heating cycle and no more than 3 heating cycles ("hits"), during which power is applied to the heating element(s) to heat the valve element and/or heat transfer element, which heating cycle(s) may have a duration of about 10 seconds each. Thus, the heat transfer element 124 can be configured in certain embodiments to provide rapid heating of the vaporizable product to achieve and maintain flowability of the vaporizable product in the product chamber 114. According to yet another embodiment, the heat transfer element 124 is configured to be heated at the position along the product flow path 118 to achieve a change in temperature at the predetermined position, as compared to prior to heating onset, of at least 50° F., at least 60° F., at least 75° F. and/or at least 100° F., in no more than 10 seconds, no more than 25 seconds, no more than 50 seconds, no more than 75 seconds, no more than 100 seconds, and/or no more than 150 seconds.

According to one embodiment, the position on the heat transfer element 124 at which the predetermined temperature is achieved is at one or more of a top end 138a of the heat transfer element and an area of the surface 140 along the length L of the heat transfer element 124 (see, e.g., FIGS. 1A-1C). For example, the position at which the predetermined temperature is achieved can extend along at least 10%, at least 25%, at least 50%, at least 75%, at least 90%, and/or at least 95% of the length L of the heat transfer element 124.

According to one embodiment, the porous valve element 126 is configured such that the at least one first porous entry surface 130 of the porous valve body 128 is configured to be heated to a predetermined temperature of at least 125° F., at least 135° F., a least 145° F., at least 150° F., at least 165° F., at least 170° F., at least 180° F., at least 195° F., at least 200° F., at least 215° F., at least 225° F., and/or at least 250° F. Furthermore, according to certain embodiments, the porous valve element is configured to be heated such that the at least one first porous entry surface 130 of the porous valve body, and/or the vaporizing surface, is heated to the predetermined temperature within a time period of no more than 10 seconds, no more than 25 seconds, no more than 50 seconds, no more than 75 seconds, no more than 100 seconds, and/or no more than 150 seconds. According to yet another embodiment, the porous valve element is configured such that a change in temperature at the at least one first porous entry surface 130 and/or vaporizing surface achieves a change in temperature as compared to prior to heating onset of at least 50° F., at least 60° F., at least 75° F. and/or at least 100° F., in no more than 10 seconds, no more than 25 seconds, no more than 50 seconds, no more than 75 seconds, no more than 100 seconds, and/or no more than 150 seconds.

Furthermore, according to certain aspects, the device 100 and/or cartridge having the heat transfer element and/or porous valve element is configured to heat the vaporizable product during operation of the device to a temperature of at least 125° F., 135° F., a least 145° F., at least 150° F., at least 165° F., at least 170° F., at least 180° F., at least 195° F., at least 200° F., at least 215° F., at least 225° F., and/or at least 250° F. The heat transfer element and/or porous valve element can be configured to heat the vaporizable product during operation of the device to such temperatures along at least 25%, at least 35%, at least 50%, at least 65%, at least 75%, at least 85% and/or at least 90% of the major flow axis through the product receiving chamber.

According to certain embodiments, the predetermined viscosity of the vaporizable product in the vicinity of the at least one first porous entry surface 130, as heated by one or more of the heat transfer element 124 and porous valve element 126, is significantly less than a room temperature viscosity of the vaporizable product. For example, the predetermined viscosity may be no more than 20 Poise, no more than 18 Poise, no more than 15 Poise, no more than 10 Poise, no more than 5 Poise, no more than 2 Poise, no more than 1.5 Poise, no more than 1.25 Poise, no more than 1 Poise, no more than 0.75 Poise, and/or no more than 0.5 Poise. For example, a viscosity of a hash material may be about 10 P when heated to a temperature of 195° F., and for a less viscous cannabidiol material, the viscosity when heated to this temperature may be about 1 P.

Returning to FIGS. 12A-12D, in one embodiment, at least a part of the at least one porous vaporizing surface 132 is a same surface that is configured to be placed in thermal contact with the at least one heating element 136. That is, a same surface at which the vaporizable product exits the porous valve body 128 may be a same surface that is in thermal contact with the at least one heating element, to provide heating at the vaporizing surface. For example, referring to the embodiment in FIGS. 12A-12D, at least a portion of the vaporizing surface 132 is on an opposing surface of the porous valve body 128 from the first porous entry surface 130. The portion of the vaporizing surface 132 is placed in contact with a heating element 136 to provide heating of the surface. In the embodiment shown in FIG. 12A, the heating element 136 is provided in contact with an interior surface portion 142 of the vaporizing surface 132 that is a part of an aperture 144 extending inside a central region of the porous valve element 126. In the embodiment shown in FIGS. 12B-12D, the portion of the vaporizing surface 132 that is opposite the porous entry surface 130 (e.g., that portion of the vaporizing surface 132 parallel to the porous entry surface 13) is placed in contact with the heating element 136, to transfer hear to the valve element 126 via that portion of the vaporizing surface 132.

According to one embodiment, the flow of the vaporizable product through the product chamber and to the porous valve element 126 can be configured to provide an optimum flow of the vaporizable product for generation of vapor for inhalation. For example, referring to FIGS. 4A-4C, the components of the cartridge 112 and/or device 100 may be configured such that a net flow direction of the vaporizable product into the at least one first porous entry surface 130 of the porous valve body 128 is aligned with and/or no more than 45° offset from a major axis of flow of the vaporizable product through the product receiving chamber. The major axis of flow may be the net direction that the product flows through the product receiving chamber, such as in a direction extending from the top end to the bottom end of the product receiving chamber 114 as shown in FIGS. 4A-4C. That is, the first porous entry surface may be substantially and even entirely perpendicular to the major axis of flow of the vaporizable product through the product chamber, and/or substantially perpendicular to a longitudinal axis A of the product chamber 114. For example, in a case where a major axis of flow of the vaporizable product is along a longitudinal direction of the product receiving chamber, and at least a portion of the at least one porous vaporizing surface of the porous valve element can be substantially perpendicular to and/or at least 45° offset from the major flow axis. Furthermore, in another embodiment, the porous valve can comprise an annular ring about a periphery of the product chamber at the lower end thereof, in which case a flow of the product may be downwards through the product chamber, and then laterally through the porous valve element surrounding the sides of the product chamber at the lower end.

Figure 10:
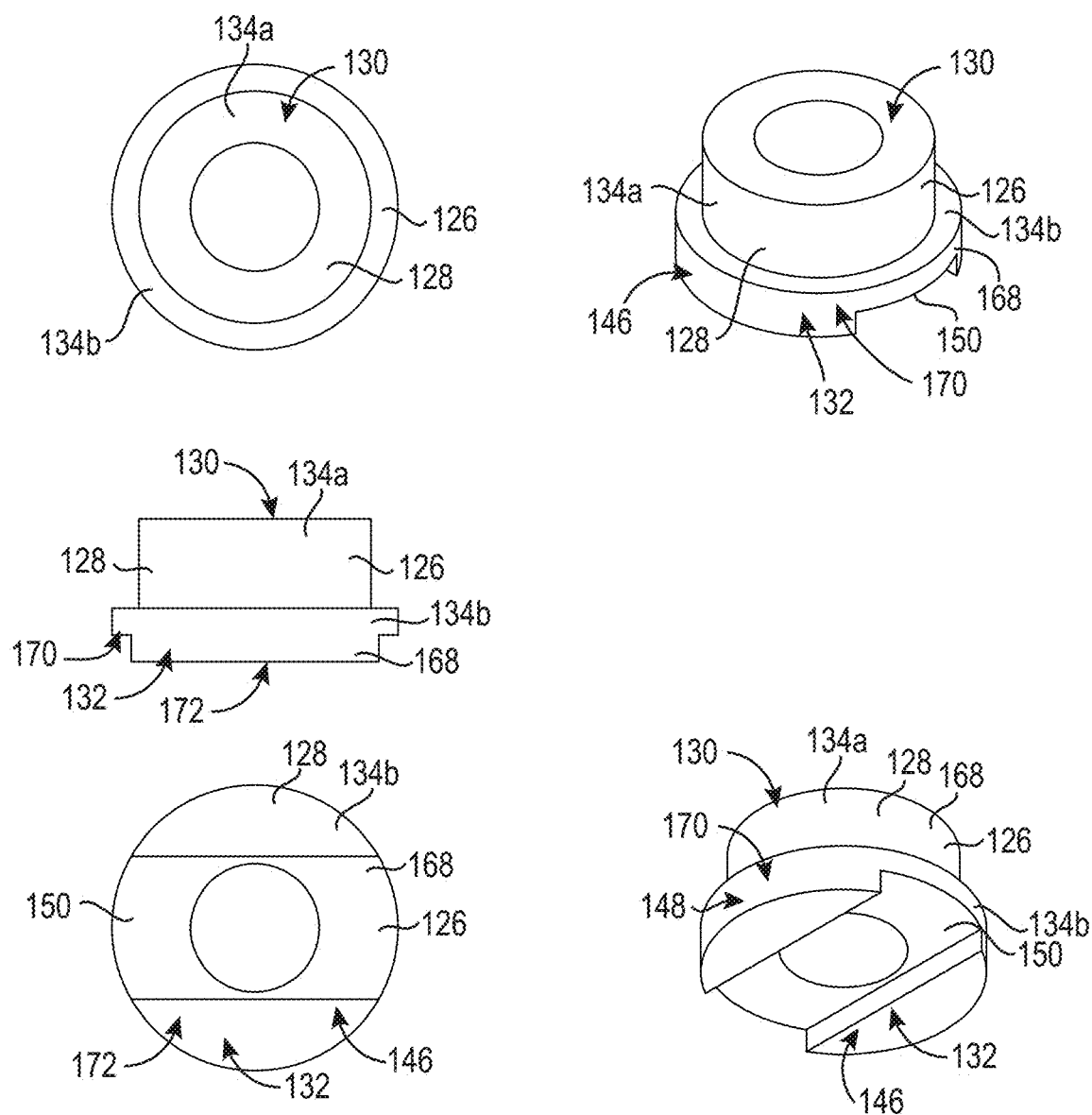
FIG. 10 depicts views of an embodiment of a porous valve element according to aspects herein.

According to certain embodiments the porous vaporizing surface 132 of the porous valve element 126 comprises a first surface 146 that is substantially perpendicular to a major axis of flow of the vaporizable product along the longitudinal direction of the product receiving chamber 114, at least a portion of which first surface 146 is configured to be placed in thermal contact with the at least one heating element 136 (see, e.g., FIG. 10). The porous vaporizing surface 132 can further comprise one or more second surfaces 148 at which the vaporizable product can exit the porous body, but which are not placed in thermal contact with the heating element 136. For example, the porous vaporizing surface 132 can comprise one or more second surfaces 148 located about a periphery of the porous valve body through which vaporizable product can exit the porous valve body.

Referring to the embodiment shown in FIG. 10, in one embodiment, wherein the first surface 146 of the porous vaporizing surface 132 that is configured to be placed in thermal communication with the at least one heating element 136 comprises one or more grooves and/or channels 150 formed therein. The grooves and/or channels 150 may facilitate exit of the vaporized product at the portion of the vaporizing surface that is contacted with the at least one heating element 136, such as for example to allow a flow path for vaporizable product away from the porous valve element. For example, according to one embodiment, the first surface 146 that is placed in thermal contact with the at least one heating element 136 may comprise an otherwise planar surface having one or more grooves and/or channels 150 formed therein. The width and length of the grooves and/or channels can be selected to provide for selected flow properties of the vaporized product and heating of the vaporizing surface 132.

The surface area of the first surface 146 that is placed in thermal contact with the heating element may also be selected to provide good heating of the porous valve element. For example, the heating element 136 may be placed in contact with a planar section of the first surface opposing the porous entry surface of the porous valve body, and may be in contact with at least 50%, at least 65%, at least 75%, at least 85%, at least 90%, at least 95%, and/or substantially the entirety of the planar opposing section of the vaporizing surface, wherein the planar section of the first surface opposing the porous entry surface has a surface area of at least 10 mm$^2$, at least 15 mm$^2$, and/or at least 18 mm$^2$. Furthermore, even in case where the first surface has channels or grooves formed therein, an area of the first surface about the grooves and/or channels that makes contact with the heating element may be at least 10 mm$^2$, at least 15 mm$^2$, and/or at least 18 mm$^2$. The dimensions of the porous valve element can also be selected to provide good heating, for example a thickness of the porous valve body as measured between the first surface of the porous vaporizing surface and the at least one first porous entry surface, is at least 1.5 mm, at least 2 mm, and/or at least 3.5 mm, and no more than 10 mm, no more than 8 mm, and/or no more than 4 mm.

According to one embodiment, at least a portion, and even the entirety, of the at least one first porous entry surface 130 of the porous valve body is configured to be exposed to the vaporizable product in the product receiving chamber 114. That is, the first porous entry surface may be in direct contact with the vaporizable product in the chamber, without any intervening layers (e.g., without a separate cotton or other wicking layer in between the surface and product), such that the product enters the entry surface 130 directly upon heating to the predetermined temperature, without passing through any other filtering or cover materials. That is, the first porous entry surface is uncovered and is in direct contact with the vaporizable product in the product chamber.

According to one embodiment, at least one of the porous valve element 126 and the heat transfer element 124 are configured to be held in a compressive relationship with the at least one heating element 136. That is, the porous valve element 126 and/or heat transfer element 124 may be pressed against the heating element 136, such that the elements exert a compressive strain on one another to maintain a fitted relationship with one another.

According to one embodiment, as shown in embodiment of FIGS. 1A-1C, the heat transfer element 124 and porous valve element 126 comprise separate structures, and may be formed of the same or different materials. According to another embodiment, the heat transfer element 124 and porous valve element 126 comprise a single unitary and/or monolithic structure formed of the same material.

Referring to the embodiments as shown in FIGS. 4A-4C, the heat transfer element 124 can extend beyond the at least one first porous entry surface 130 of the porous valve body, such as into an interior region 152 of the product receiving chamber 114. In one embodiment, the heat transfer element 124 can extend along a central axis A of the product chamber, such as along the major flow axis of product through the product receiving chamber. In yet another embodiment, the heat transfer element 124 can extend along the exterior of the product chamber 114, such as adjacent to or as a part of the sidewalls 112 defining the product chamber 114. According to one embodiment, the heat transfer element may extend along at least 25%, at least 35%, at least 50%, at least 65%, at least 75%, at least 85%, and/or at least 90% of the major flow axis through the product receiving chamber. A length of the product receiving chamber along the major flow axis, according to certain aspects, can be at least at least 10 mm, at least 15 mm, and/or at least 20 mm, such as about 22 mm. In the embodiments as shown in FIGS. 4A-4C, the heat transfer element 124 extends along substantially the entire length of the product chamber 114, from a position close to the upper end 120a of the product chamber, to at least the porous valve element 126. In the embodiments as shown in FIGS. 4A-4C, the heat transfer element 124 further extends through a central aperture 144 in the porous valve element 126 to allow thermal contact of the bottom end 138b of the heat transfer element with a heating element 136 to heat the heat transfer element 124.

According to certain embodiments, the porous valve body 128 of the porous valve element 126 comprises a porous material that provides suitable heat transfer characteristics to heat the vaporizable product in the product receiving chamber 114. For example, according to one embodiment, the porous valve element 126 comprises a porous body 128 having a porous material comprising at least one selected from the group consisting of porous glass, porous ceramic, porous quartz, and porous sintered metal. As yet another example, the porous valve element 126 can comprise a porous body 128 having a porous material comprising at least one selected from the group consisting of porous borosilicate glass, porous alumina, and porous silicon carbide. As yet another example, the porous valve element 126 can comprise a porous body 128 having a porous material comprising porous borosilicate glass. According to certain aspects, the porous valve body 128 may be formed of a material having a sufficiently high thermal conductivity, to provide for heating of the valve body 128 and transfer of heat to the vaporizable product. In one embodiment, the porous valve body comprises a porous material having a thermal conductivity of at least 0.5 W/m*K, at least 0.8 W/m*K, at least 1 W/m*K, at least 1.15 W/m*K, and/or at least 1.2 W/m*K. In yet a further embodiment, the thermal conductivity may be at least 10 W/m*K, at least 15 W/m*K, at least 30 W/m*K, at least 50 W/m*K, and/or at least 70 W/m*K. According to certain embodiments, the thermal conductivity of the porous valve body 128 may be less than 300 W/m*K, less than 200 W/m*K, less than 100 W/m*K, less than 50 W/m*K, less than 25 W/m*K, less than 10 W/m*K, and/or less than 5 W/m*K. For example, the thermal conductivity may be in the range of from 0.5 to 5 W/m*K, such as 1.0 to 2.0 W/m*Km, and/or may be in a range of from 10 to 50 W/m*K, such as from 15 to 27 W/m*K, and/or may be in a range of from 50 to 200 W/m*K, such as from 70 to 170 W/m*K. Furthermore, according to certain aspects, the porous valve body 128 can comprise a specific heat of less than 1200 J/kg*K, less than 1000 J/kg*K, and/or less than 900 J/kg*K, and greater than 500 J/kg*K, greater than 750 J/kg*K, and/or greater than 800 J/kg*K.

Examples of materials and parameters that may be suitable for the porous valve body 128 are provided in Table I below.

TABLE I

| Porous Material | Thermal Conductivity (W/m * K) | Specific Heat (J/kg * K) |
| --- | --- | --- |
| Porous Borosilicate Glass | 1.2 | 830 |
| Porous Alumina Ceramic | 15-27 | 880 |
| Porous Silicon Carbide Ceramic | 70-170 | 750 |

By way of comparison, cotton has a thermal conductivity of 0.03 W/m*K, and a specific heat of 1300-1500 J/kg*K.

According to certain aspects, a porosity of the porous valve body 128 and/or the pore size of the porous valve body may be selected to provide for a flow of the vaporizable product through the porous valve element. For example, a porosity of the porous valve element may be at least 25%, at least 35%, and/or at least 50%, and less than 95%, less than 85% and/or less than 75%. As another example, the pore size may be selected such that the porous valve body has an average pore size of at least 2 microns, at least 3 microns, at least 4 microns, at least 5 microns, at least 8 microns, and/or at least 10 microns, and less than 25 microns, less than 18 microns, less than 16 microns, less than 10 microns and/or less than 8 microns. As another example, the average pore size may be in the range of from 2 microns to 20 microns, such as from 2 microns to 8 microns, and even from 3 to 6 microns, such as from 4 microns to 5.5 microns, and as another example may be in the range of from 8 microns to 20 microns, such as from 10 microns to 16 microns. The porosity and/or pore size may also be selected at least in part in relation to a vaporizable product to be used in the device. For example, in the case of a thicker and/or more viscous product, such as hash, the porosity and/or pore size may be selected to be on the larger side, to provide for a suitable flow of the material through the porous valve element. As another example, in the case of a less viscous product, such as distillate, a lower porosity and/or pore size may be selected to control flow through the porous valve body.

According to certain embodiments, the heat transfer element 124 comprises a material selected to provide suitable thermal characteristics for the transfer of heat to the vaporizable product in the chamber 114. According to certain aspects, the heat transfer element 124 is substantially non-porous and/or has a porosity that is less than that of the porous valve body 128. The heat transfer element 124 can also be selected of the same or a different material than the porous valve body. For example, according to certain embodiments, the heat transfer element comprises at least one selected from a glass, a ceramic, and a metal. As yet another example, the heat transfer element can comprise a material corresponding to at least selected from the group consisting of alumina, silicon carbide, stainless steel, titanium, aluminum, graphite and aluminum nitride. In yet another example, the heat transfer element can comprise a material corresponding to at least one selected from the group consisting of alumina and silicon carbide. In one embodiment, the heat transfer element 124 can comprise a body having a thermal conductivity of at least 0.5 W/m*K, at least 0.8 W/m*K, at least 1 W/m*K, at least 1.15 W/m*K, and/or at least 1.2 W/m*K. For example, the thermal conductivity may be at least 10 W/m*K, at least 15 W/m*K, at least 30 W/m*K, at least 50 W/m*K, at least 70 W/m*K, at least 100 W/m*K, at least 125 W/m*K, at least 150 W/m*K and/or at least 160 W/m*K. According to certain embodiments, the thermal conductivity of the heat transfer element 124 may be less than 300 W/m*K, less than 200 W/m*K, less than 100 W/m*K, less than 50 W/m*K, and/or less than 25 W/m*K. For example, a thermal conductivity of the heat transfer element 124 may be in the range of from 10 to 300 W/m*K, such as from 10 to 35 W/m*K, and even 15 to 27 W/m*K, such as from 50 to 200 W/m*K, including 70 to 170 W/m*K, such as from 10 to 20 W/m*K, including about 12-16 W/m*K, such as from 20 to 30 W/m*K, including 23 to 26 W/m*K, such as from 160 to 245 W/m*K, including 164-237 W/m*K, such as from 160-175 W/m*K, including 165 to 170 W/m*K, and/or such as from 130 to 195 W/m*K, including 140 to 180 W/m*K. Furthermore, according to certain embodiments, the heat transfer element comprises a body having a specific heat of less than 1200 J/kg*K, less than 1000 J/kg*K, and/or less than 900 J/kg*K, and greater than 500 J/kg*K, greater than 750 J/kg*K, and/or greater than 800 J/kg*K.

Examples of materials and parameters that may be suitable for the heat transfer element 124 are provided in Table II below.

TABLE II

| Heat Transfer Element Material | Thermal Conductivity (W/m * K) | Specific Heat (J/kg * K) |
| --- | --- | --- |
| Alumina Ceramic (99%) | 15-27 | 880 |
| Silicon Carbide Ceramic | 70-170 | 750 |
| Stainless Steel | 14 | 502 |
| Titanium | 25 | 544 |
| Aluminum | 164-237 | 921 |
| Graphite | 168 | 720 |
| Aluminum Nitride | 140-180 | 740 |

Furthermore, according to certain embodiments, the materials suitable for the heat transfer element 124 may also be suitable for use as the material for the porous valve body when provided in a porous form.

According to certain embodiments, the material used for the heat transfer element and/or porous valve element 126 may be selected according to heat transfer characteristics suitable for the vaporizable product being used. For example, for a thicker and/or more viscous product, such as hash, a material may be used for one or more of the heat transfer element and/or porous valve element that has higher heat transfer properties, such as a higher thermal conductivity, whereas a material having lower heat transfer properties such as lower thermal conductivity may be used in case where the product is less thick and/or has a lower viscosity, such as for cannabidiol and/or distillate. Examples of suitable combinations for different product types are provided in Table III below, although the possible combinations of materials/structures encompassed herein is not limited to the examples below.

TABLE III

| Product Type (Cartridge Type) | Porous Valve Element Material | Porosity | Pore Size (microns) | Heat Transfer Element Material | Heat Transfer Element Structure |
| --- | --- | --- | --- | --- | --- |
| Cannabidiol (Cartridge C) | Porous Borosilicate | 50% | 4-5.5 | Alumina | 4 Fins |
| Distillate (Cartridge D) | Porous Borosilicate | 50% | 4-5.5 | Alumina | Bulge |
| Hash (Cartridge H) | Porous Borosilicate | 50% | 10-16 | Silicon Carbide | 4 Fins |

Referring to the embodiments of FIGS. 3A-3C, 4A-4C and 6A-6C, according to certain aspects, the heat transfer element 124 comprises an elongate heat-conducting column 154 that extends along a predetermined length L of the vaporizable product receiving chamber 114. In these embodiments as shown, the elongate heat-conducting column 154 is disposed within the product chamber 114. In other embodiments, the elongate heat-conducting column is disposed externally to the product chamber 114, and/or comprises one or more sidewalls 122 of the vaporizable chamber 114. The elongate heat-conducting column 154 may heat the product along the product flow path to reduce the viscosity and/or at least partially melt the product, for example to maintain flowability of the product in the chamber.

Referring to FIGS. 3A-3C, according to certain embodiments, the structure and configuration of the elongate heat-conducting column 154 can be selected to provide predetermined heat characteristics with the product chamber 114. For example, referring to FIGS. 3A and 3C, according to one embodiment, the elongate heat-conducting column comprises a plurality of fins 156 extending radially outwardly from a central axis C of the elongate heat-conducting column. For example, the elongate heat-conducting column can comprises 4 fins that are positioned substantially equidistant about the central axis C of the elongate heat-conducting column, and that extend outwardly from the central axis of the elongate heat conducting column, and where the fins further extend longitudinally along a length of the column and/or product receiving chamber 114. The fins 156 may provide an increased surface area structure that provides greater thermal contact with the vaporizable product as it passes through the product chamber. The shape and size of the fins can also be selected in accordance with desired heating characteristics, as well as in relation to the material used for the column and product characteristics. For example, referring to FIG. 3A, which may be an embodiment suitable for a cannabidiol product, the fins may extend a significant distance down the length of the column, as compared to FIG. 3C depicting an embodiment suitable for a hash product, where a higher thermal conductivity column may have fins that terminate slightly more highly above the end of the column, to provide a space above the porous valve element. Other configurations of the fins may also be provided, including more or fewer fins, shorter fins, longer fins, thicker or thinner fins, etc. Also, alternate high surface area structures other than fins can be provided, such as spiral features or projections that extend from the column 154. In one embodiment, the plurality of fins extend at least 25%, at least 50%, at least 75%, at least 80% and/or at least 95% along the length of the product receiving chamber, to provide heating of the product in the product chamber. Furthermore, according to certain embodiments, the plurality of fins comprise portions that extend at least 25%, at least 50%, at least 75%, at least 85% and/or at least 95% of a cross-sectional width of the product receiving chamber, such as across a diameter of the product receiving chamber.

Referring to FIG. 3B, in one embodiment, the elongate heat-conducting column 154 comprises a first section 158 comprising bulging portion 160 along a central axis of the elongate heat-conducting column 154, the bulging portion 160 comprising a greater radius from the central axis than one or more second sections 162 along the central axis of the elongate heat conducting column. The building portion 160 may serve to extend the column into the product flow path such that the vaporizable product is brought into contact with the column as it flows through the product chamber to heat the vaporizable product. The embodiment as shown in FIG. 3B may be suitable, for example for a lower viscosity material, such as distillate, which is to be heated but may not require as high of temperatures as cannabidiol or hash to flow through the porous valve element. Furthermore, in certain embodiments, the bulging portion 160 may only extend along a section of the product flow path in the chamber, and may not extend along the entire flow path. For example, the bulging portion 160 may be located towards the lower end of the column in a bottom section of the product chamber, so as to provide heating of the product before the product comes into contact with the porous valve element.

In one embodiment, referring to FIGS. 3A-3C and FIGS. 4A-4C, the elongate heat-conducting column 154 can comprises a neck region 164 towards the bottom end 138b of the column 154, and configured to be proximate to the porous valve element, along the central axis of the column. According to certain aspects, the neck region 164 has a thinner diameter than other regions of the column 154 along the central axis of the heat conducting column. According to some embodiments the neck region may provide less heating of the product in that region, for example to control a temperature of the product flowing from the upper end 120a of the product chamber towards the porous valve element 126, such that the product achieves the predetermined viscosity in the vicinity of the porous valve element. For example, the neck region may allow the product to cool slightly such that the flow of the product into the porous valve element can be controlled. In one version, the neck region 164 comprises a region where the elongate heat-conducting column tapers in diameter from a first maximum diameter to a second maximum diameter than is smaller than the first at the neck region proximate the porous valve element. For example, a diameter of the fins 156 may taper down to the diameter of a central column body 166 from which they extend, as shown in FIGS. 3A and 3B. In one embodiment, the elongate heat conducting column has a diameter or at least 2.5 mm, at least 3 mm and/or at least 3.5 mm proximate a base of the elongate heat conducting column and a diameter at a neck region of less than 4 mm, less than 3 mm and/or less than 2.5 mm. A length of the neck region may also be relatively small in comparison to a length of the column having the fins and/or other protruding region.

Without being limited to any one particular embodiment for any particular product, it is noted that FIGS. 2A-2B, 3A, 4B, 5B, 6B, 7B, 8B, and 9C, depict embodiments that may be suitable for a vaporizable product comprising cannabidiol. FIGS. 3B, 4C, 5C, 6C, 7C, 8C, and 9B, depict embodiments that may be suitable for a vaporizable product comprising distillate. FIGS. 3C, 4A, 5A, 6A, 7A, 8A and 9A depict embodiments that may be suitable for a vaporizable product comprising hash. However combinations of these structures may also be provided, and the structures may also be used with any vaporizable product.

Referring to FIGS. 4A-4C and 10, in one embodiment, the porous valve element 126 comprises an annular fitting 168 having a first or upper portion 143a comprising the porous entry surface 130, and which is configured to fit within the one or more walls 122 defining the product chamber 114. In one embodiment, the annular fitting 168 can further comprise a second or lower portion 143a that is configured to extend beyond the end of the one or more walls 122, such that the vaporized product can exit the chamber in a lateral direction via peripheral surfaces 170 of the lower portion. Alternatively and/or additionally, the vaporized product may exit the chamber through a base surface 172 of the annular fitting, where both the bottom surface and/or peripheral surfaces may form portions of the vaporizing surface 132 of the porous valve element. According to one embodiment, the second portion 143a of the porous valve body may have a peripheral region with a diameter greater than that of the first portion, wherein the vaporizable product travels through the first portion of the porous valve element to the second portion and the vapor formed from the vaporizable product exits the porous valve element through the one or more of a peripheral surface of the peripheral region, or through the surface 172 formed on the bottom of the second portion. According to yet another embodiment, the annular fitting 168 can comprise a single portion having substantially the same diameter throughout the thickness thereof, such as a disc-like ring, where the fitting 168 can either be fitted entirely within the sidewalls of the product chamber, or can at least partly extend from the product chamber. Furthermore, which an annular or ring-like fitting is described and shown, the porous valve element is not limited thereto, and may comprise further shapes, such as cuboid shapes or other shapes, and may be sized to accommodate a shape and/or structures within the product chamber, which may comprise a circular cross-section or other shapes, such as a rectangular cross-section or an irregular cross-sectional shape.

According to one embodiment, referring to FIG. 10 and FIGS. 4A-4C, the porous valve element can comprise an annular fitting 168 having a central aperture 144 formed therethrough (e.g. through a thickness thereof), wherein the central aperture 144 forms a reservoir 174 configured to receive the vaporizable product therein. For example, product flowing towards the porous valve element can collect in the reservoir 174 and may enter the porous valve body via one or more interior surfaces 176 on the interior of the aperture 144. The flow of the product into the porous valve body may thus be through porous entry surface 132 comprising the interior surface portion 176 and a top surface portion 178 that is perpendicular to the flow of the product through the chamber. According to one embodiment, the heat transfer element can comprises an elongate column having a bottom end or base 138b configured to fit through aperture 144 in the valve, such that it can be placed in thermal contact with the at least one heating element 136. The sides of the lower portion of the column can define the reservoir in cooperation with the internal surfaces of aperture in the porous valve element. Also, the heat transfer element can comprise one or more annular stopper rings 180 or other features that can be placed flush with the interior surfaces of the aperture, such as to block a flow of product through the aperture 144 and out of the chamber.

Referring to the embodiments of FIGS. 12A-12D, according to certain aspects, the heat transfer element 124 and porous valve element 126 are configured to be heated by the same heating element 136 or by different heating elements.

Figure 12A:
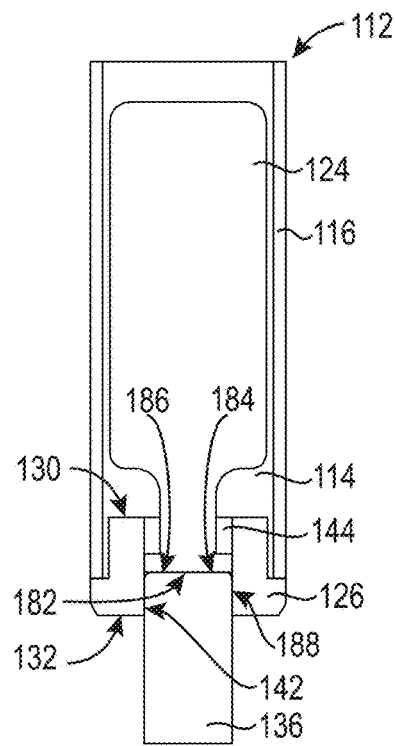
FIGS. 12A-12D are cross-sectional views of different embodiments of cartridges and heating elements to heat the cartridges, according to aspects herein.
Figure 12B:
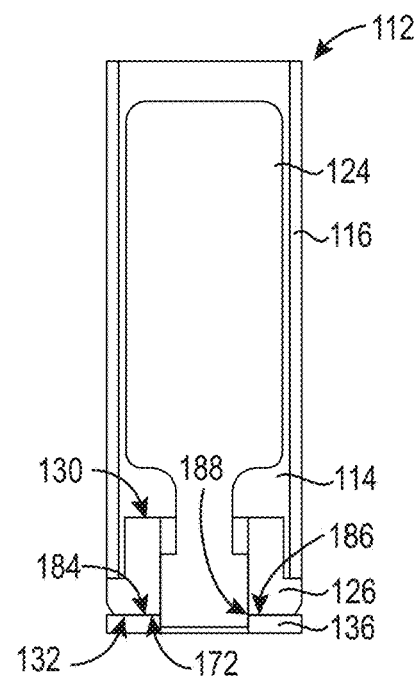

For example, in the embodiments as shown in FIGS. 12A-12B, both the heat transfer element 124 and porous valve element 126 are heated by the same heating element, by being placed in thermal communication (e.g., direct physical contact) with the heating element 136. In the embodiment as shown in FIG. 12A, the bottom surface 182 of the heat transfer element is placed in direct contact with a surface 184 of a heating element 136, such as an upper surface 186 of a heating rod, and the interior portions 176 of the vaporizing surface 132 of the valve element, within the valve aperture, are contacted with a surface 184 corresponding to the side surface portions 188 of the heating element such as the side surfaces of the heating rod contacting the heat transfer element. Thus, the heat transfer element and porous valve element may be simultaneously heated by the same heating element. In the embodiment as shown in FIG. 12B, the heat transfer element comprises a side surface 190 that is placed in contact with a side surface portion 188 of the surface of a heating plate 136, the upper surface 186 of which heating plate is placed in contact with the bottom portion 172 of the vaporizing surface such that the porous valve element and heat transfer element are simultaneously heated by the heating plate. In the embodiment as shown in FIG. 12B, the heating plate comprises a donut shape, to at least partially encircle the base of the heat transfer element. As an alternative, the heating element 136 can comprise a heating plate that has an upper surface 186 that contacts the bottom surfaces of both the porous valve element and heat transfer element, to transfer heat thereto.

Figure 12C:
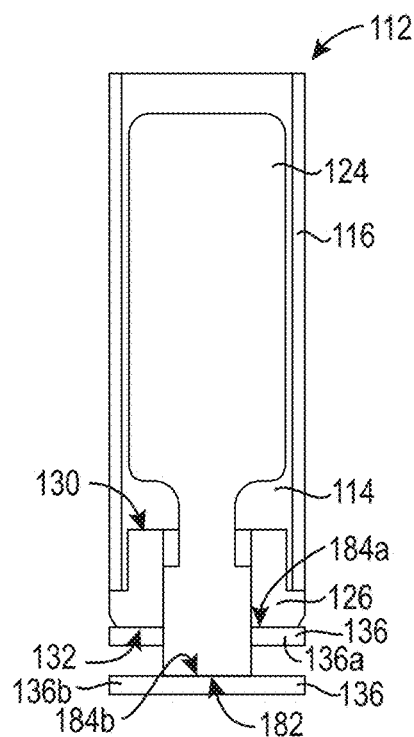
Figure 12D:
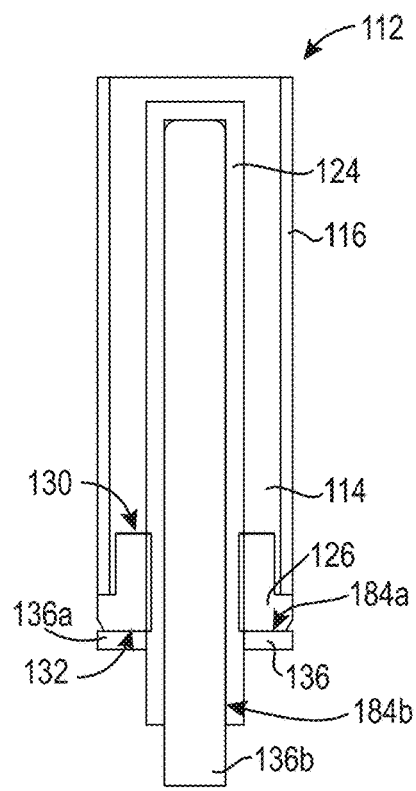

According to yet another embodiment, as shown in FIGS. 12C-12D, the porous valve element and heat transfer element are heated by separate first and second heating elements 136a, 136b. For example, according to certain embodiments, the porous valve element is configured to be heated by a first heating element 136a in thermal contact with the vaporizing surface of the porous valve element, and heat transfer element is heated by a second heating element 136b in contact with a base surface of the heat transfer element that is at a same side of the device as the vaporizing surface of the porous valve element, as shown for example in FIG. 12C. For example, the first heating element may be a donut shaped heating plate that surrounds a periphery of the base of the heat transfer element and contacts the bottom portion of the vaporizing surface with an upper surface thereof, whereas the second heating element can comprise a plate with an upper surface placed in contact with the end surface of the heat transfer element. In the embodiment as shown in FIG. 12D, a first heating element 136a can comprise a donut shaped plate heater as in FIG. 12C, but the second heating element 136b can comprise a rod heater inserted into a ceramic sheath comprising the heat transfer element. That is, according to one embodiment, the porous valve element can be heated by a first heating element in thermal contact with the vaporizing surface of the porous valve element, and the heat transfer element can be heated by a second heating element that extends along an internal length of the heat transfer element. Other configurations of heating elements and configurations of contact with the porous valve element and heat transfer element can also be provided that are other than those specifically described and/or shown herein. Furthermore, the one or more heating elements 136 can comprise a variety of different heating elements, including one or more of a rod heater, a ring heater, a disc heater, a plate heater, a coil heater, a pancake coil (see, e.g., FIG. 17), and/or the first and second heating elements are external or internal to one or more of the porous valve element and/or heat transfer element.

According to certain embodiments, the vaporizable product used in the device 100 and/or cartridge 112 can be any one or more of a liquid, a wax and/or a material that is substantially solid at room temperature. For example, the vaporizable product comprises any one or more of hash, cannabidiol, and a cannabis oil distillate.

Figure 11A:
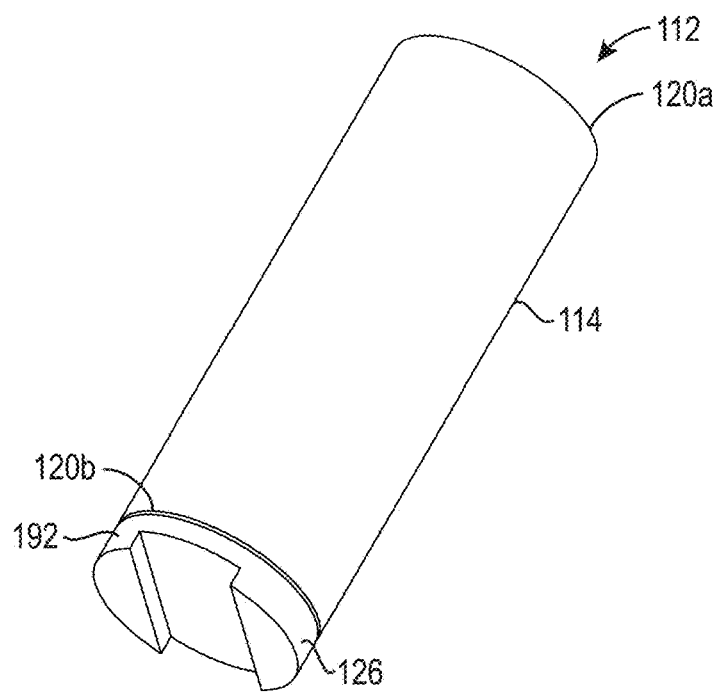
FIGS. 11A-11C depict isometric, and cross-sectional views of embodiments of cartridges according to aspects herein.
Figure 11B:
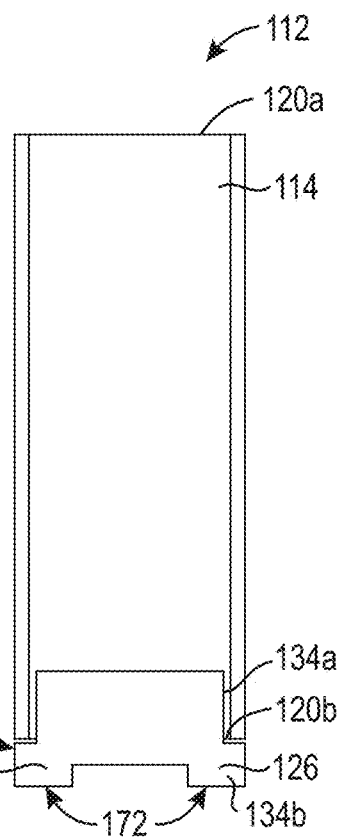
Figure 11C:
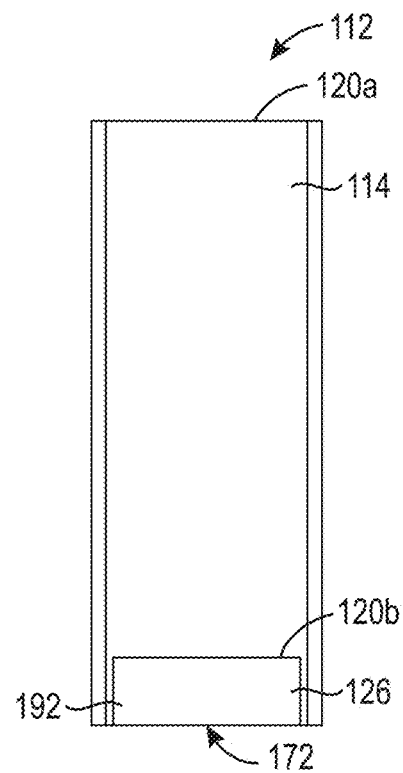

Referring to the embodiment as shown in FIGS. 11A-11B, according to certain aspects, a portable vaporizing device and/or cartridge may be provided that does not include a heat transfer element such as a heat conducting column, but instead provides heating via the porous valve element 126. For example, as shown in FIGS. 11A-11C, the porous valve element can comprise a disc-like fitting at a lower end 120b of the product chamber 114. Similarly to the annular fitting described with respect to FIGS. 4A-4C above, the disc-like fitting can in certain embodiments comprise upper and lower portions 134a, 134b, where the lower portion 134b extends beyond the walls of the chamber and can have a diameter greater than that of the upper portion, and the vaporizing surface 132 includes both a bottom portion 172 and peripheral portions 170 through which vaporized product can exit the product chamber via the porous valve element, as shown in FIG. 11B. In another embodiment, the disc-like fitting is sized to fit within the annular walls of the chamber, and comprises a bottom surface 172 that acts as the vaporizing surface 132 to pass vapor therethrough, as shown in FIG. 11C. As another embodiment, the disc-like fitting may serve as a stopper to close the bottom opening of the product chamber. The disc-like fitting may also comprise grooves and/or channels 150 formed in the vaporizing surface thereof, to promote the passage of vaporized product away from the vaporizing surface, as discussed elsewhere herein for other embodiments of the porous valve element.

Referring to FIGS. 11A-11C, according to one embodiment of a portable vaporizing device and/or cartridge that uses the porous valve element as the source of heating of the vaporizable product (e.g., without a heat transfer element), the device and/or cartridge comprises the vaporizable product receiving chamber 114 configured to receive the vaporizable product therein, the vaporizable product receiving chamber comprising one or more chamber walls 122 defining a product flow path between upper and lower opposing ends of the vaporizable product receiving chamber, and the porous valve element 126 located towards the lower end 120b of the vaporizable product receiving chamber that is configured to heat the vaporizable product to the predetermined viscosity. The porous valve element can comprise the porous valve body comprising porous material configured to allow heated vaporizable product having the predetermined viscosity to pass therethrough.

According to certain embodiments, the porous valve further comprises at least one exposed first porous entry surface of the porous valve body that is configured to be placed in direct thermal contact with vaporizable product in the product chamber to transfer heat thereto. The at least one first porous entry surface is configured to receive the heated vaporizable product from the product flow path into the porous valve body. In one embodiment, the exposed first porous entry surface comprising a porous material having a thermal conductivity of at least 0.5 W/m*K to allow for adequate heating of the exposed first porous entry surface 130 and heating of the product in thermal contact with the exposed first porous entry surface 130. As similarly discussed above, by "exposed" surface it is meant that the first porous entry surface is in direct contact with the vaporizable product in the chamber, without any intervening layers, such that the product enters the entry surface 130 directly upon heating to the predetermined temperature, without passing through any other filtering or cover materials. That is, the first porous entry surface is uncovered and is in direct contact with the vaporizable product in the product chamber.

According to certain embodiments, the at least one porous vaporizing surface is configured to flow the heated vaporizable product therethrough such that the vaporizable product is at least partially vaporized in the vicinity of the at least one porous vaporizing surface while exiting the porous valve body. Furthermore, referring to FIGS. 11A-11C, a portion (e.g., the bottom portion 172) of the at least one porous vaporizing surface is on a side of the porous valve body opposite the first porous entry surface, and the portion of the at least one porous vaporizing surface is configured to be placed into direct contact with at least one heating element to provide heating of the porous valve element during operation of the portable vaporizing device.

The portable vaporizing device and/or cartridge having the product chamber and porous valve element 126 (e.g., without the heat transfer element 124) can comprise any of the other features, characteristics, parameters and/or structures otherwise described herein, such as any described herein with respect to FIGS. 1A-10 and 12A-14B. For example, in one embodiment, the bottom portion of the vaporizing surface of the porous valve element may be placed in a compressed relationship with at least one heating element, such as a heating plate and/or heating ring. As another example, the porous valve element may also be capable of being heated to any of the temperatures and/or at the heating rates described elsewhere herein as being obtainable therewith, and/or to achieve the predetermined viscosities described elsewhere herein. As yet another example, the porous valve element can comprise any of the materials or properties described elsewhere herein, such as for example a porous borosilicate material.

According to one embodiment, a method of using the portable vaporizing device and/or cartridge comprises heating the porous valve element and flow path heat transfer element to flow the product through the product chamber and pass the vaporizable product through the porous valve element and generate a vapor therefrom, and inhaling the generated vapor. The method can also optional comprise providing a cartridge comprising product to a portable vaporizing device, and operating the device, such as by providing power to the one or more heating elements, to heat the porous valve element and flow path heat transfer element to cause the vaporizable product through the porous valve element and generate a vapor therefrom. In a case where the portable vaporizing device and/or cartridge comprises the porous valve element but does not include a heat transfer element, the method can include simply heating the porous valve element to flow the product through the product chamber and pass the vaporizable product through the porous valve element and generate a vapor therefrom, and inhaling the generated vapor. According to yet another embodiment, a method of manufacturing a cartridge for a vaporizable product, can comprise at least partly and even entirely filling the product chamber of the cartridge and/or device described herein with the vaporizable product.

Figure 13A:
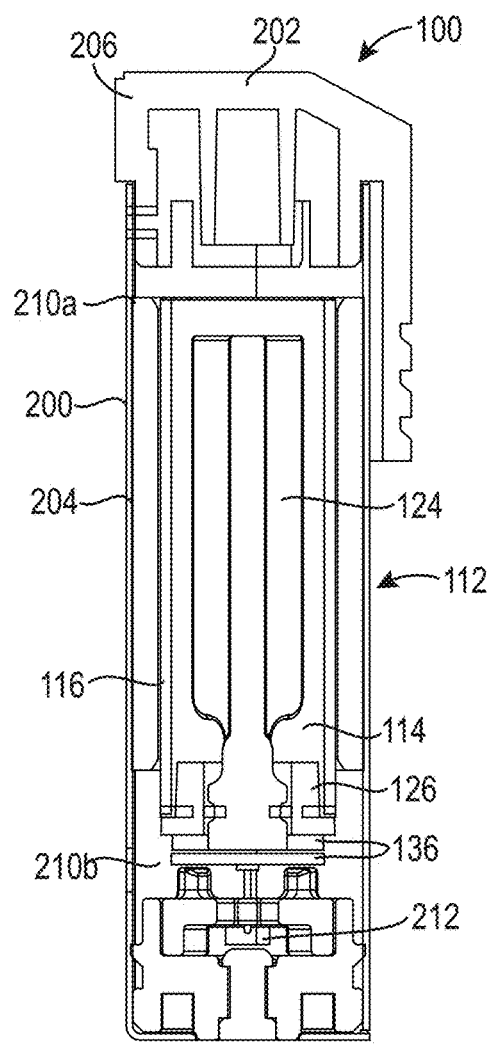
FIGS. 13A-13B are sectional views of a vaporizing device suitable for use with a cartridge according to aspects herein.
Figure 13B:
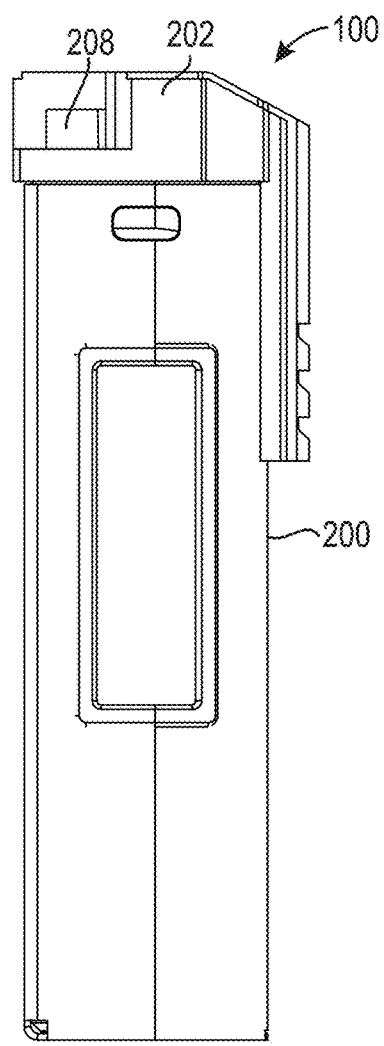
Figure 14A:
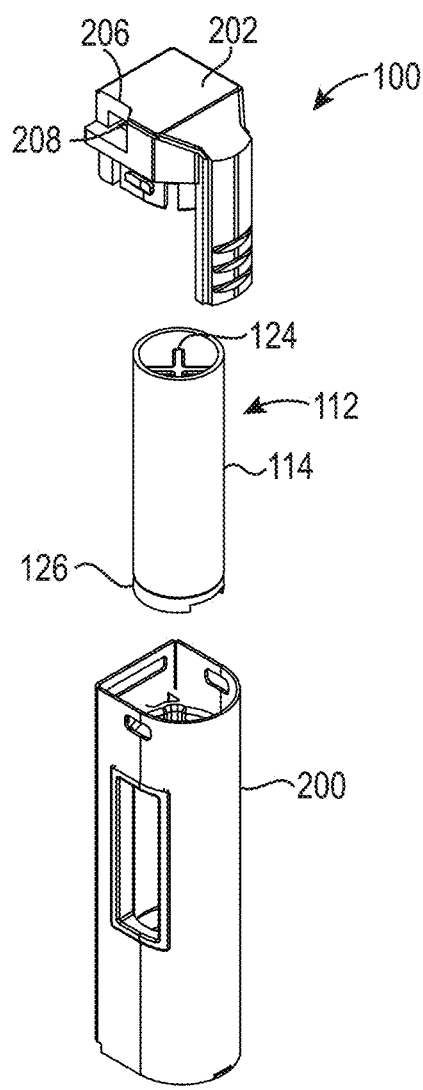
FIGS. 14A-14B are exploded views of a vaporizing device suitable for use with a cartridge according to aspects herein.
Figure 14B:
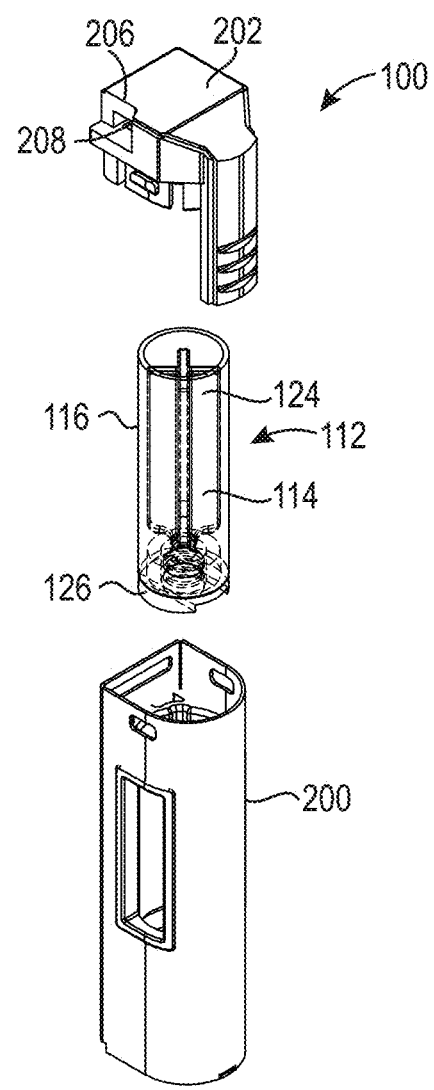

Referring to FIGS. 13A-13B and 14A-14B, embodiments of a portable vaporizing device 100 comprising the product chamber 114 and porous valve element 126, and optionally with the heat transfer element 124, is described. For example, the portable vaporizing device 100 may be configured to receive a removable single-use or refillable cartridge 112 comprising the product chamber 114 and porous valve element 126, with optional heat transfer element, such as any of those disclosed herein. Referring to FIG. 13A, in one embodiment, the device comprises a housing 200 that is configured to accommodate the product chamber and porous valve element (and optionally heat transfer element) therein. For example, the housing 200 can be configured to accommodate a cartridge 112 therein, with an openable cap 202 portion that can be opened or closed to refill the housing with fresh cartridges.

According to one embodiment, the portable vaporizing device further comprises a gas flow chamber 204 configured to receive vaporized product exiting the product chamber 114 via the porous valve element 126, and direct the vaporized product towards a mouthpiece 206 (e.g., in the cap 202) comprising an inhalation outlet 208 that allows for inhalation of the vaporized product. In one embodiment, the gas flow chamber 204 is external to the product chamber 114, and re-directs a flow of vaporized product from a bottom end 210b of the gas flow chamber 204 where product is received from the vaporizing surface of the porous valve element, to a top end 210a of the gas flow chamber 204 to flow the vaporized product to the mouthpiece 206. In one embodiment, the gas flow chamber 204 is external to and laterally surrounds the product chamber 114. For example, the gas flow chamber 204 may be at least partly defined by the space in between the sidewalls 212 of the housing, and the product chamber sidewalls 122, to form a conduit therebetween for the passage of vaporized product. In one embodiment, the gas flow chamber 204 is configured to receive vaporized product exiting the porous valve element in a lateral direction, and re-direct the flow of vaporized product upwardly and external to the product chamber to the mouthpiece.

In certain embodiments, the portable vaporizing device may also comprise a power source 212, such as a battery configured to provide power to the heating element(s) 136 to cause the heating element(s) to heat during operation of the device. In one embodiment, operation of the device, such as by pushing a switch, causes power to be delivered to the heating elements during a heating cycle, which may for example by about 10 seconds, to vaporize the product. According to yet another embodiment, the device 100 comprises one or more heating elements that may be permanently or semi-permanently affixed therein, and where the device is configured to receive a cartridge such that the surfaces of the porous valve element and/or heat transfer element that are to be heated are placed in direct physical contact with the one or more heating elements. The device may also be capable of providing the heating elements in compressed relation with respect to the porous valve element and/or heat transfer element, such that a close fit can be provided.

The portable vaporizing device and/or cartridge may thus be capable of providing good vaporization of product to provide an enhanced experience therewith.

EXAMPLES

In the present example, three different cartridge types were assembled and tested to determine a heating efficiency and profile for the heat transfer element provided in each cartridge, and for the heating of the product type provided in the cartridge. Cartridges C, D and H having the porous valve element and heat transfer element reported in Table III above were filled with cannabidiol product, distillate product, and hash product, respectively. The cartridges were subjected to heating cycles of about 10 seconds each (about 7-10 seconds heating followed by 7-10 seconds of "cooling"), and the temperatures at the top end of the heat transfer element in each cartridge were measured before, during and after each cycle.

Figure 15:
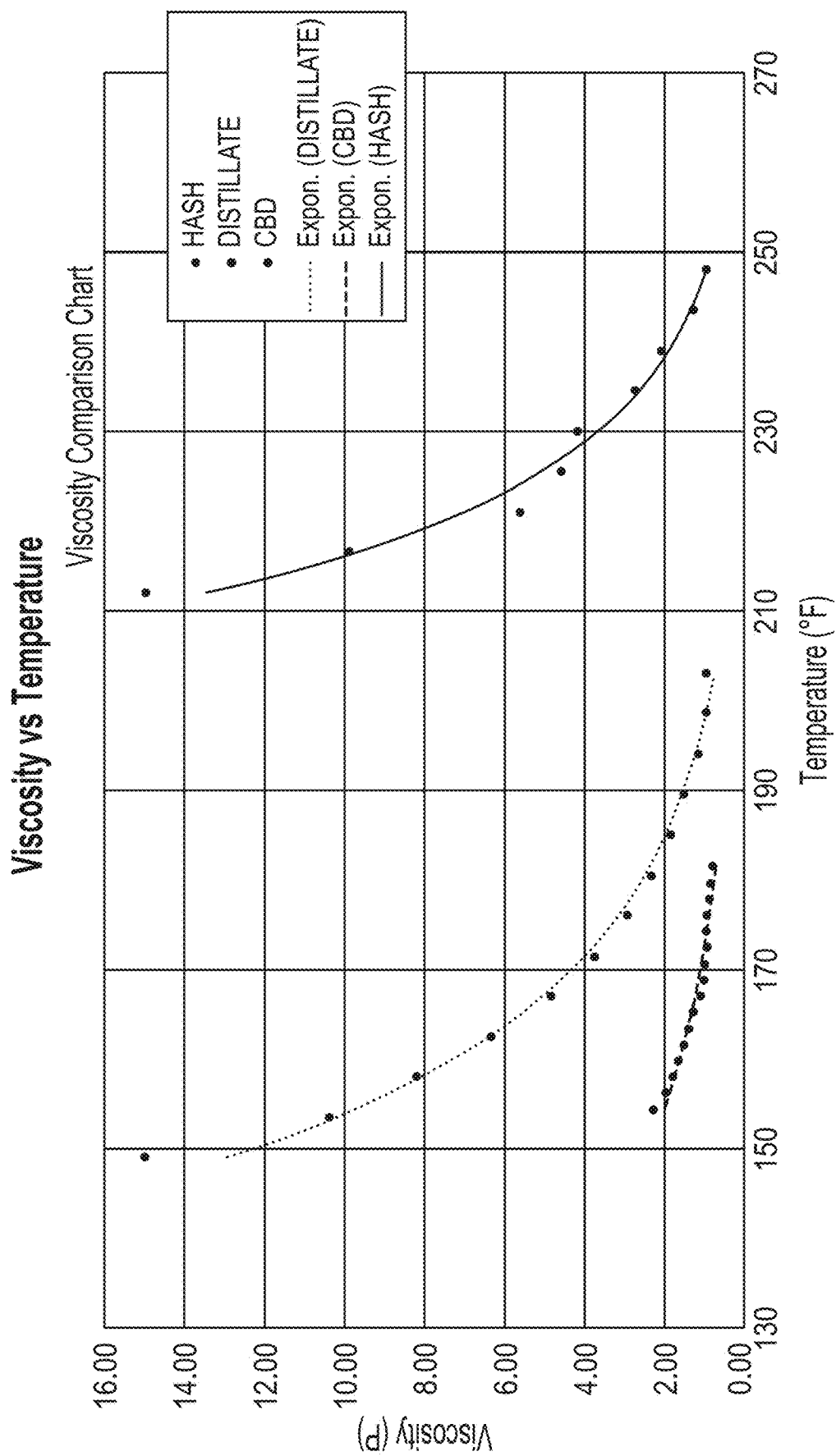
FIG. 15 is a graph showing change in viscosity for increasing temperature for hash, distillate and cannabidiol.
Figure 16:
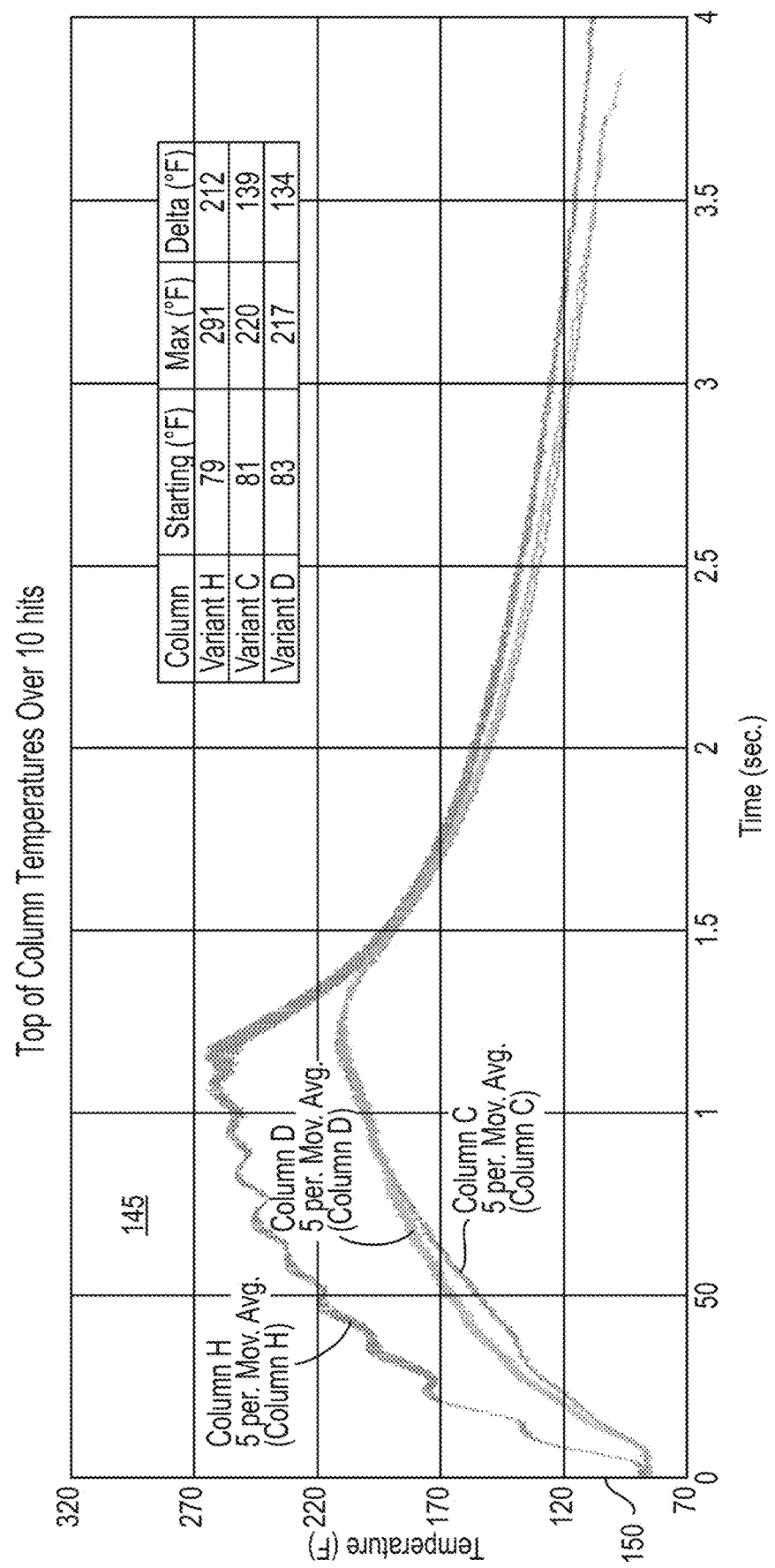
FIG. 16 is a graph showing temperature over time for heating in different embodiments of cartridges according to aspects herein.
Figure 17:
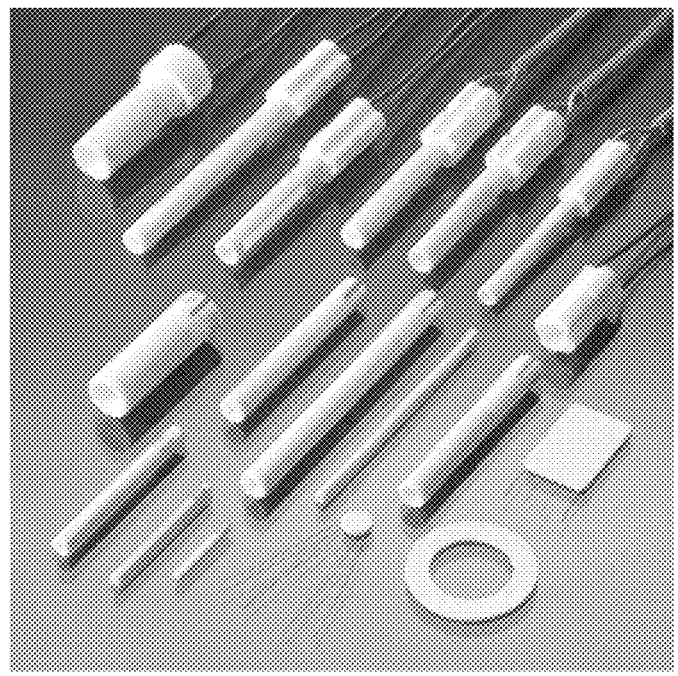
FIG. 17 depicts embodiments of heating elements suitable for use with a vaporizing device according to aspects herein.
Figure 17:
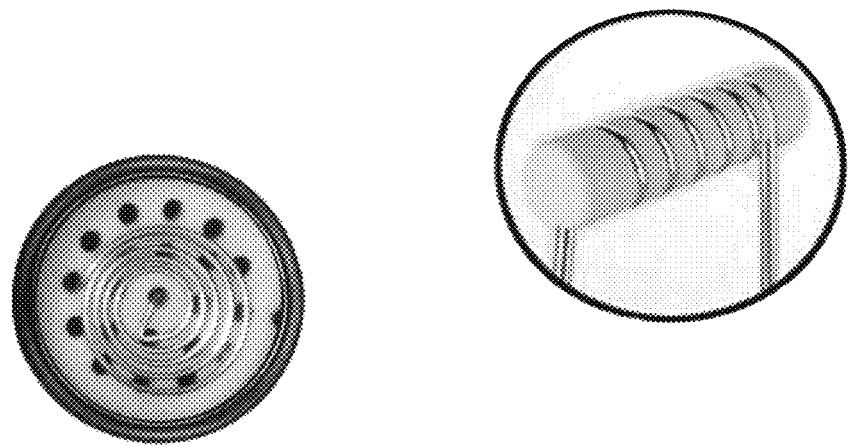
Figure 18:
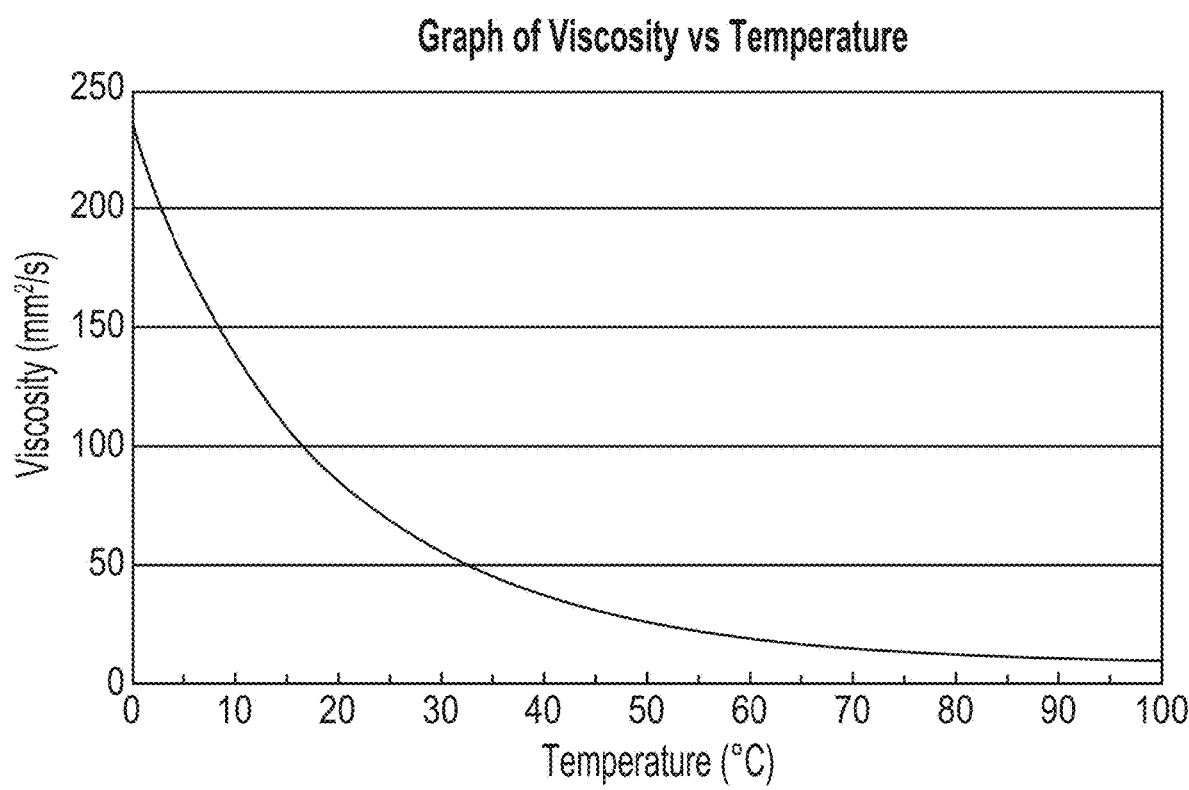
FIG. 18 is a graphical representation of a substance's viscosity in relation to temperature.
Figure 19:
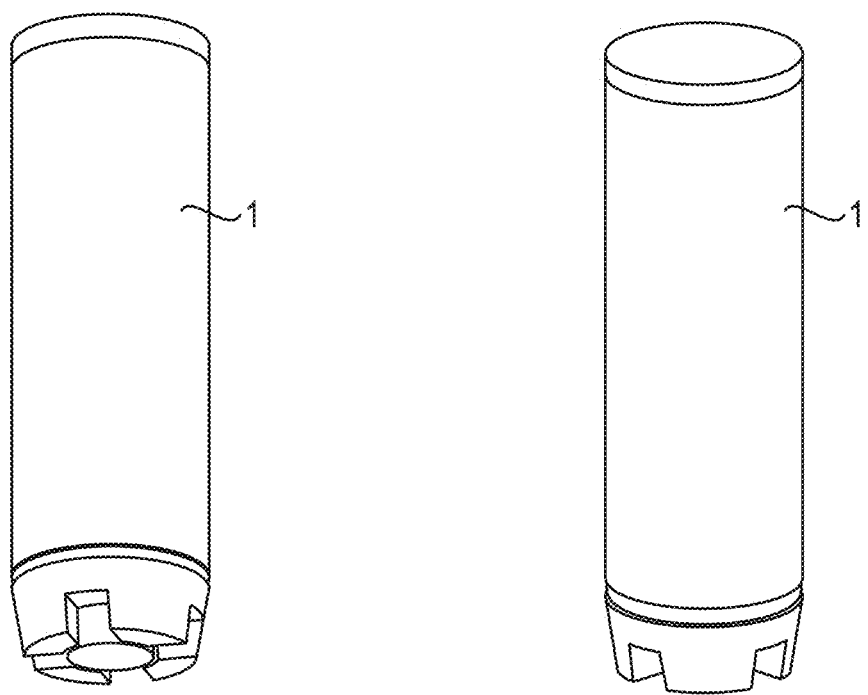
FIG. 19 is a front perspective view of the cartridge according to an embodiment of the present invention.
Figure 20:
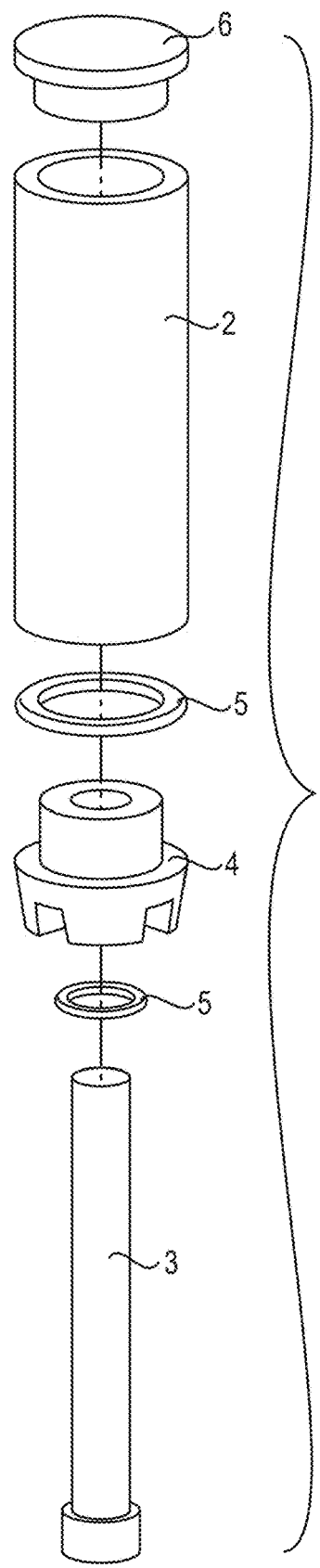
FIG. 20 is an exploded view of the cartridge according to an embodiment of the present invention.
Figure 21:
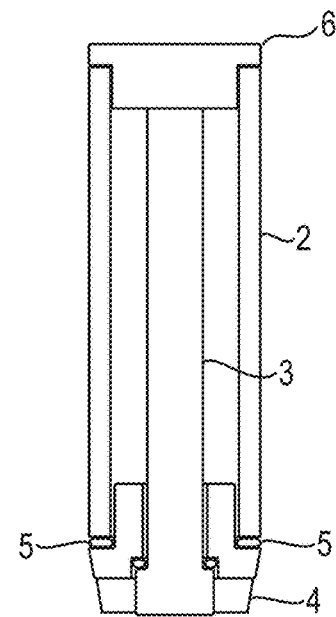
FIG. 21 is a schematic view of the cartridge according to an embodiment of the present invention.
Figure 22:
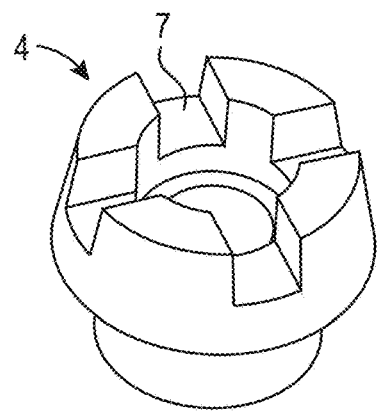
FIG. 22 shows an embodiment of wick and grooves.
Figure 23:
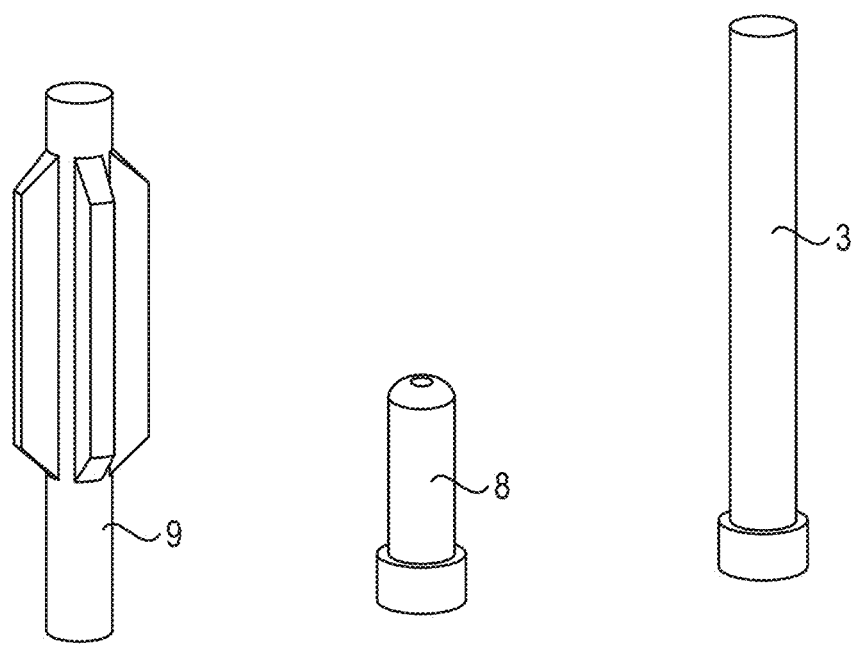
FIG. 23 shows a perspective view of embodiments of the center column.
Figure 24:
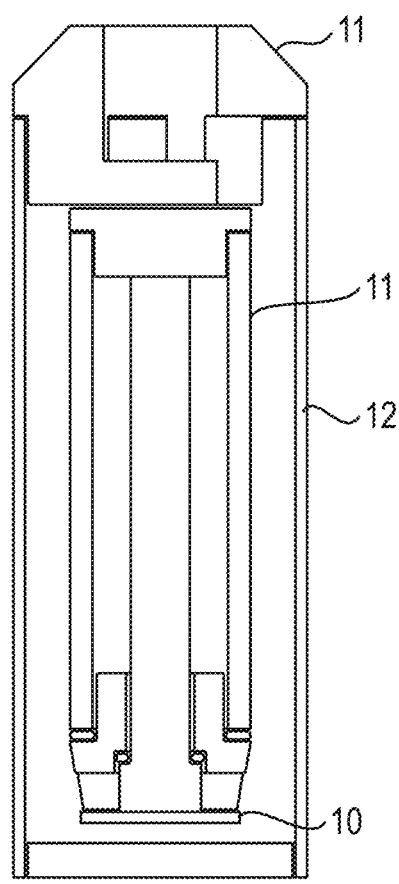
FIG. 24 is a schematic view of an embodiment of the invention showing the mouthpiece, heating element, and cartridge.

As can be seen from FIG. 17, the cartridge H containing hash product and using a silicon carbide heat transfer element achieved a temperature after a first heating cycle of about 130° F., a second cycle of over 170° F., with increasing temperatures with each cycle, indicating that the heat transfer element retained heat over the cycles. A maximum temperature reached during the 10 cycles that were performed as 291° F., with an overall change in temperature from the starting temperature of 212° F. The cartridge C containing cannabidiol product and using an alumina heat transfer element achieved a somewhat lower temperature after a first heating cycle of a little under 120° F., a second cycle of over 120° F., with increasing temperatures with each cycle, indicating that the heat transfer element retained heat over the cycles. A maximum temperature reached during the 10 cycles that were performed as 220° F., with an overall change in temperature from the starting temperature of 139° F. The cartridge D containing distillate product and using an alumina heat transfer element similarly achieved a somewhat lower temperature after a first heating cycle of a little under 120° F., a second cycle of over 120° F., with increasing temperatures with each cycle, indicating that the heat transfer element retained heat over the cycles. A maximum temperature reached during the 10 cycles that were performed as 217° F., with an overall change in temperature from the starting temperature of 134° F. Accordingly, the cartridge and/or device can be devised with different heat transfer element materials and/or structures, to provide a predetermined heating profile for heating and/or vaporizing of a product contained in the product chamber. For example for a very thick and viscous material such as hash, a higher thermal conductivity material such as silicon carbide can be used, to provide sufficient heating of the hash product to render it sufficiently flowable. For less viscous and/or thinner materials, such as distillate and/or cannabidiol, a lower thermal conductivity material such as alumina can be used, so as to provide sufficient flow characteristics without exceeding a predetermined rate of flow through the porous valve element (e.g., without causing excess flow resulting in leakage of the product liquid form as opposed to vaporized form from the porous valve element). Furthermore, FIG. 15 shows a comparison of the change in viscosity for increasing temperature for hash, distillate and cannabidiol, showing that reduced viscosities can be obtained at much lower temperatures for cannabidiol and distillate as compared to hash.

Specific embodiments are further described below.

Referring to FIGS. 18-24, according to one embodiment the oil to be vaporized is housed in a container, reservoir, or cartridge (1) consisting of a tube (2) or extruded hollow shape and sealed on its proximal end with a wick (4); an embodiment may also include a ceramic column (3) running through both the wick (4) and the tube (2); an embodiment may also include silicone or cotton seals (5) between the wick and tube and also between the wick and center column; an embodiment may also include a cap (6) sealed to the tube (2) on the opposite end form the wick (4).

The porous wick (4) can be made of a ceramic foam or porous glass (quartz or borosilicate), and the column (3) can be made of a metal, glass, or ceramic material. Additionally, to begin the vaporization process a heat supply is required, referred to as the heating element (10), but also includes any heat source or heated surface.

In one embodiment of the design the interaction between the wick (4), column (3) and the heat source is a key aspect to the functionality of this invention. The heating element (10), which can be made of any conductive material, is in contact with both the wick (4) and column (3), transferring heat to both. The heating element can either be assembled together with the wick, column, and tube or it can exist as a separate part to be moved in and out of contact. If the heating element is a separate part it can be effective when in contact with the interior or the exterior of the wick, while in contact with the column. Heat transfer also occurs from the heating element through the wick (4) and into the column (3).

In one embodiment the wick (4) transfers heat to the oil within the container. Oil in contact with the heated wick will decrease in viscosity, allowing it to flow through the wick via capillary action and gravity. In one embodiment of the design the wick (4) has grooves (7) on the face contacting the heat source. This increases the area of exposed heating element where vaporization occurs, resulting in increased vapor production.

Depending on the viscosity of the oil a center column (3) may not be required, however for thicker oils a center column is needed and may vary in geometry depending on oil viscosity. The center column may have two functions, increase flow rate to the heat source and reduce wasted oil in the container that may be trapped in the tube opposite from the heat source.

In one embodiment, the center column (3) comes in direct contact with the heat source. As heat spreads through the center column within the container, heat transfers to the oil causing it to melt and flow. An important design element can be the center column within the container near the wick. Decreased viscosity just before entering the wick increases flow rate to the heating element which can create more vapor. In an embodiment of the invention a short center column (8) can be used to increase flow rate just before entering the wick.

Thicker or crystalized substances require more heat to reach a wickable viscosity. This can be achieved by increasing the surface area between the center column (3) and the oil. In an embodiment of the invention the center column is a rod in the center of the tube (2). Various rod lengths and diameters may be used to increase the surface contact between the center column and oil. In an embodiment of the invention, the center column may contain fins (7) that extend to the container inner wall. These fins increase the surface area and allow heat to transfer to the oil more efficiently.

An embodiment of an application of this invention includes the cartridge (1) assembled in to a heating chamber (12) containing a heating element (10). The vaporization process is activated by this heating element when current is applied to it, the current is provided by a battery that is connected to the heating element (10) and attached to the heating chamber (12). Heat is transferred through the wick and column and into the oil container, decreasing the viscosity of the solid oil substance so that it can move through the container and be absorbed by the wick. The liquefied oil is absorbed into the wick by capillary action and gravity, where it is then vaporized and inhaled through a mouthpiece (11) that is attached to the heating chamber (12).

Regarding the wick (4), it has been determined that a pore size of 10-160 micrometers with porosity of 40-60% may be effective for movement of liquid materials via capillary action. During testing, pore sizes above 160 micrometers may allow too high a flow rate of oil, and result in poor vapor production due to an oversaturation of the heat supply source. Tests performed with pore sizes below 10 micrometers in certain instances did not allow a high enough oil flow rate. However, the pore size may vary depending on the viscosity of the substance.

Accordingly aspects of the invention add the capability of vaporizing organic solid oil substances without additives using a wicking system. Embodiments may replace current designs, providing both oil storage and oil delivery activated by heat.

What is claimed is:

1. A portable vaporizing device comprising:
   a vaporizable product receiving chamber configured to receive a vaporizable product therein, the vaporizable product receiving chamber comprising one or more chamber walls defining a product flow path between upper and lower opposing ends of the vaporizable product receiving chamber;
   an elongate heat-conducting column disposed interior to the one or more chamber walls within the vaporizable product receiving chamber and extending at least partly along the product flow path, the elongate heat-conducting column being configured to transfer heat to the vaporizable product received in the vaporizable product receiving chamber to at least partially melt or reduce the viscosity of vaporizable product as it flows via gravitational pull from the upper end to the lower end along the product flow path; and
   a porous valve element defining a bottom surface of the vaporizable product receiving chamber, the porous valve element being located towards the lower end of the vaporizable product receiving chamber and external to the elongate heat-conducting column, the porous valve element comprising:
      a porous valve body comprising porous material configured to allow heated vaporizable product having a predetermined viscosity to pass therethrough;
      at least one first porous entry surface of the porous valve body configured to receive the heated vaporizable product from the product flow path into the porous valve body; and
      at least one porous vaporizing surface of the porous valve body configured to flow the heated vaporizable product out of the porous valve body,
   wherein the elongate heat conducting column comprises a base surface configured to be placed in direct physical contact with one or more heating surfaces of one or more heating elements, and the at least one porous vaporizing surface of the porous valve element is configured to be placed in direct physical contact with the one or more heating surfaces of the one or more heating elements, and wherein the elongate heat conducting column passes through the porous valve element to directly physically contact the one or more heating surfaces of the one or more heating elements,
   wherein the direct physical contact between the at least one porous vaporizing surface and the base surface, with the one or more heating surfaces of the one or more heating elements, provides conductive heating of both of the elongate heat conducting column and porous valve element during operation of the portable vaporizing device to heat the vaporizable product to the predetermined viscosity, and
   wherein the porous valve element is configured to be heated by the one or more heating elements to cause the heated vaporizable product having the predetermined viscosity from the product receiving chamber to flow into and through the porous valve body, and to cause the heated vaporizable product to at least partially vaporize in the vicinity of the at least one porous vaporizing surface while exiting the porous valve body.

2. The device according to claim 1, wherein a net flow direction of the vaporizable product into the at least one first porous entry surface of the porous valve body is aligned with a major axis of flow of the vaporizable product through the product receiving chamber.

3. The device according to claim 1, wherein the at least one porous vaporizing surface that is configured to be placed in direct physical contact with the one or more heating surfaces of the one or more heating elements comprises a substantially planar surface having one or more grooves and/or channels formed therein.

4. The device according to claim 1, wherein at least a portion of the at least one first porous entry surface of the porous valve body is configured to be exposed to the vaporizable product in the vaporizable product receiving chamber.

5. The portable vaporizing device according to claim 1, wherein the porous valve element comprises a porous valve body having a porous material comprising at least one selected from the group consisting of porous glass, porous borosilicate, porous ceramic, and porous quartz.

6. The portable vaporizing device according to claim 5, wherein the porous valve element comprise a porous valve body having a porous material comprising porous borosilicate glass.

7. The portable vaporizing device according to claim 1, wherein the porous valve element comprises a porous valve body having a porosity of from 40% to 60%.

8. The portable vaporizing device according to claim 1, wherein the porous valve element comprises a porous valve body having a pore size of from 10 micrometers to 160 micrometers.

9. The portable vaporizing device according to claim 1, wherein the elongate heat-conducting column comprises at least one selected from the group consisting of metal, glass and ceramic material.

10. The portable vaporizing device according to claim 1, wherein the device is a refillable cartridge.

11. The portable vaporizing device according to claim 1, wherein the device is configured to receive a refillable cartridge or single use cartridge comprising the vaporizable product receiving chamber, and wherein the device further comprises a mouthpiece configured to receive the vapor that exits the vaporizable product receiving chamber via the porous valve element.

12. The portable vaporizing device according to claim 1, wherein the elongate heat-conducting column comprises a plurality of fins extending radially outwardly from a central axis of the elongate heat-conducting column.

13. The portable vaporizing device according to claim 12, wherein the elongate heat-conducting column comprises 4 fins that are positioned substantially equidistant about the central axis of the elongate heat-conducting column, and that extend outwardly from the central axis of the elongate heat conducting column, and wherein the fins further extend longitudinally along a length of the product receiving chamber.

14. The portable vaporizing device according to claim 1, wherein the elongate heat-conducting column comprises a base configured to fit through an aperture in the porous valve body, to be placed in direct physical contact with the one or more heating elements.

15. The portable vaporizing device according to claim 1, wherein the elongate heat-conducting column and porous valve element are configured to be heated by the same heating element.

16. The portable vaporizing device according to claim 1, wherein the porous valve element is configured to be heated by a first heating element in thermal contact with the at least one porous vaporizing surface of the porous valve element, and the elongate heat-conducting column is configured to be heated by the first heating element in direct physical contact with the base surface of the elongate heat-conducting column that is at a same side of the device as the at least one porous vaporizing surface of the porous valve element.

17. The portable vaporizing device according to claim 1, wherein the one or more heating elements comprise a plate heater, and wherein the one or more heating elements are external to the porous valve element and elongate heat-conducting column.

18. The portable vaporizing device according to claim 1, wherein the porous valve element is located radially external to the elongate heat-conducting column.

19. A method of using the portable vaporizing device according to claim 1, comprising:
heating the porous valve element and elongate heat-conducting column to flow the product through the vaporizable product receiving chamber and pass the vaporizable product through the porous valve element and generate a vapor therefrom; and
inhaling the generated vapor.

20. The portable vaporizing device according to claim 1, wherein the device comprises:
a gas flow chamber configured to receive vaporized product exiting the vaporizable product receiving chamber via the porous valve element, and direct the vaporized product towards a mouthpiece comprising an inhalation outlet that allows for inhalation of the vaporized product,
wherein the gas flow chamber is external to and at least partly laterally surrounds the vaporizable product receiving chamber.

21. The portable vaporizing device according to claim 1, wherein the porous valve element comprises a unitary porous valve body having the at least one first porous entry surface and the at least one porous vaporizing surface, such that the heated vaporizable product flows continuously through the unitary porous valve body from the at least one first porous entry surface to the at least one porous vaporizing surface.

* * * * *